US005861290A

United States Patent [19]
Goldsmith et al.

[11] Patent Number: 5,861,290
[45] Date of Patent: Jan. 19, 1999

[54] METHODS AND POLYNUCLEOTIDE CONSTRUCTS FOR TREATING HOST CELLS FOR INFECTION OR HYPERPROLIFERATIVE DISORDERS

[76] Inventors: Mark A. Goldsmith, 20 Maple St., West Roxbury, Mass. 02132; Robert O. Ralston, 2863 Judah, San Francisco, Calif. 94122

[21] Appl. No.: 965,039

[22] Filed: Oct. 22, 1992

Related U.S. Application Data

[63] Continuation of Ser. No. 461,461, Jan. 17, 1990, abandoned, which is a continuation-in-part of Ser. No. 300,637, Jan. 23, 1989, abandoned.

[51] Int. Cl.$^6$ .......................... C12N 15/09; C12N 15/11; C12N 15/63; C12N 15/86
[52] U.S. Cl. .................. 435/172.3; 424/93.2; 435/320.1; 514/44; 536/23.1; 536/23.2; 536/23.5; 536/23.53; 536/23.6; 536/23.7; 536/23.72; 536/24.1; 536/24.5
[58] Field of Search ............................ 435/172.3, 320.1; 424/93 A, 93.2; 514/44; 536/23.1, 23.2, 23.5, 23.53, 23.6, 23.7, 23.72, 24.1, 24.5

[56] References Cited

U.S. PATENT DOCUMENTS

| | | | |
|---|---|---|---|
| 4,405,712 | 9/1983 | Vande Woude et al. | 435/5 |
| 4,603,112 | 7/1986 | Paoletti et al. | 435/235.1 |
| 4,650,764 | 3/1987 | Temin et al. | 435/350 |
| 4,663,281 | 5/1987 | Gillies et al. | 435/69.1 |
| 4,708,818 | 11/1987 | Montanier et al. | 435/5 |
| 4,725,669 | 2/1988 | Essex et al. | 530/322 |
| 4,738,922 | 4/1988 | Haseltine | 435/172.3 X |
| 4,769,330 | 9/1988 | Paoletti et al. | 435/172.3 |
| 4,861,719 | 8/1989 | Miller | 435/236 |
| 4,868,116 | 9/1989 | Morgan et al. | 435/373 |
| 4,980,289 | 12/1990 | Temin et al. | 435/235.1 |
| 5,026,635 | 6/1991 | Ferguson et al. | 435/5 |
| 5,091,309 | 2/1992 | Schlesinger et al. | 435/69.1 |
| 5,192,553 | 3/1993 | Boyse et al. | 424/529 |
| 5,246,924 | 9/1993 | Fox et al. | 514/50 |
| 5,304,489 | 4/1994 | Rosen | 435/320.1 |
| 5,399,346 | 3/1995 | Anderson et al. | 424/93.21 |

FOREIGN PATENT DOCUMENTS

| | | |
|---|---|---|
| B-19201/88 | 1/1987 | Australia . |
| 0 178 220 A2 | 4/1986 | European Pat. Off. . |
| 0 273 782 A1 | 7/1988 | European Pat. Off. . |
| 288163 | 10/1988 | European Pat. Off. . |
| 0 293 181 A1 | 11/1988 | European Pat. Off. . |
| 0 334 301 A1 | 9/1989 | European Pat. Off. . |
| 0 361 749 A1 | 4/1990 | European Pat. Off. . |
| 0 386 882 A1 | 9/1990 | European Pat. Off. . |
| 440 219 A1 | 8/1991 | European Pat. Off. . |
| 2 559 159 | 2/1984 | France . |
| 2 606 060 | 10/1986 | France . |
| WO 86/00922 | 2/1986 | WIPO . |
| WO 89/01972 | 3/1989 | WIPO . |
| WO 89/01973 | 3/1989 | WIPO . |
| WO 89/02468 | 3/1989 | WIPO . |
| WO 89/05345 | 6/1989 | WIPO . |
| WO 89/05349 | 6/1989 | WIPO . |
| WO 89/07150 | 8/1989 | WIPO . |
| WO 90/01870 | 3/1990 | WIPO . |
| WO 90/02806 | 3/1990 | WIPO . |
| WO 91/11092 | 10/1990 | WIPO . |
| WO 93/02556 | 2/1993 | WIPO . |

OTHER PUBLICATIONS

Nelson et al., "Gene replacement therapy for inborn errors of purine metabolism," Cold Spring Harbor Symp. Quant. Biol., 51(2): 1065–1071 (1986).

Pizer et al., "A mammalian cell line designed to test the mutagenic activity of anti–herpes nucleosides," Int. J. Cancer, 40: 114–121 (1987).

Maxwell, et al., "Regulated Expression of A Transfected Toxin Gene" Abstract No. N93, J. Cell. Biochem., 0 (10 Part D): 39 (1986).

Maxwell, et al., "HTLV–Regulated Expression of a Transfected Diphtheria Toxin Gene," Abstract No. P314, J. Cell., Biochem., 0 (11 Part D): 67 (1987).

Harrison, et al., "Toward HIV–Regulated Expression of A Diphtheria Toxin A Gene In Transfected Cells," Abstract No. G418, J. Cell. Biochem., 0 (13 Part B): 302 (Jan. 21, 1989).

Aldovini et al., "Humoral and Cell–Mediated Immune Responses to Live Recombinant BCG–HIV Vaccines," Nature, 351:479–482 (1991).

Altmann et al., "Contransfection of ICAM–1 and HLA–DR Reconstitutes Human Antigen–Presenting Cell Function in Mouse L Cells," Nature, 338:512–514 (1989).

Ameisen et al., "Cell Dysfunction and Depletion in AIDS: The Programmed Cell Death Hypothesis," Immunology Today, 12:102–105 (1991).

Anderson et al., "Gene Expression in Implanted Rat Hepatocytes Following Retroviral–Mediated Gene Transfer," Som. Cell and Mol. Genetics, 15:215–227 (1989).

Anderson, W.F., "Prospects for Human Gene Therapy," Science, 226:401–409 (1984).

Armentano et al., "Effect of Internal Viral Sequences on the Utility of Retroviral Vectors," J. Virology, 61:1647–1650 (1987).

(List continued on next page.)

Primary Examiner—Jonny F. Railey, II
Attorney, Agent, or Firm—Norman J. Kruse; Donald J. Pochopien; Robert P. Blackburn

[57] ABSTRACT

Host cells may be treated for an infection or a hyperproliferative disorder which is characterized by the presence, in the affected cells, of a trans-acting factor capable of regulating gene expression by inserting into the cells a polynucleotide construct having a cis-acting regulatory sequence which is regulated by the trans-acting factor and an effector gene which renders said cell susceptible to protection or destruction. For example, the cis-acting region may be homologous to the HIV tar region, and the effector gene may encode ricin A or HSV-1 thymidine kinase. Upon infection with HIV, the HIV tat protein activates the tar region, and induces transcription and expression of ricin A, resulting in cell death, or of HSV-1 tk, resulting in cell death upon treatment with dideoxynucleoside agents such as acyclovir and gancyclovir.

81 Claims, 5 Drawing Sheets

OTHER PUBLICATIONS

Arnold et al., "Vaccine Development for Aids Through Molecular Surgery of a Human Common Cold Virus Surface," *J. Cell. Biochem.,* L401:145 (1990).

Barnd et al., "Specific, Major Histocompatibility Complex–Unrestricted Recognition of Tumor–Associated Mucins By Human Cytotoxic T Cells," *Proc. Nat'l Acad. Sci., USA,* 86:7159–7163 (1989).

Berkner, K.L., "Development of Adenovirus Vectors for the Expression of Heterologous Genes," *BioTechniques,* 6:616–629 (1988).

Bernards et al., "Effective Tumor Immunotherapy Directed Against an Oncogene–Encoded Product Using a Vaccinia Virus Vector," *Proc. Nat'l Acad. Sci., USA,* 84:6854–6858 (1987).

Bernards et al., "N–myc Amplification Causes Down–Modulation of MHC Class I Antigen Expression in Neuroblastoma," *Cell,* 47:667–674 (1986).

Bix et al., "Rejection of Class I MHC–Deficient Haemopoietic Cells by Irradiated MHC–Matched Mice," *Nature,* 349:329–331 (1991).

Bolognesi et al., "Prospects of Treatment of Human Retrovirus–Associated Diseases," *Cancer Research (Suppl.)* 45:4700s–4705s (1985).

Braakman et al., "ICAM–Melanoma Cells Are Relatively Resistant To CD3–Mediated T–Cell Lysis," *Int. J. Cancer,* 46:475–480 (1990).

Braciale et al., "Antigen Presentation Pathways to Class I and Class II MHC–Restricted T Lymphocytes," *Immunology Reviews,* 98:95–114 (1987).

Bubenik et al., "Local Administration of Cells Containing an Inserted IL–2 Gene and Producing IL–2 Inhibits Growth to Human Tumors in nu/nu Mice," *Immunology Letters,* 19:279–282 (1988).

Buseyne et al., "Detection of HIV–Specific Cell–mediated Cytotoxicity in the Peripheral Blood from Infected Children," *J. Immunology,* 150(8):3569–3581 (1993).

Butini et al., "Comparative Analysis of HIV–Specific CTL Activity in Lymphoid Tissue and Peripheral Blood," *J. Cell. Biochem. (Suppl.)* 18B:147 (*Abstract J306*) (1994).

Carey, J., "Human Gene Therapy: After a Lot of Looking, Now the Leap," *Business Week,* Science & Technology, pp. 133 & 136 (May 1, 1989).

Carmichael et al., "Quantitative Analysis of the Human Immunodeficiency Virus Type 1 (HIV–1)–Specific Cytotoxic T Lymphocyte (CTL) Response at Different Stages of HIV–1 Infection: Differential CTL Responses to HIV–1 and Epstein–Barr Virus in Late Disease," *J. Exp. Med.,* 177:249–256 (1993).

Carr et al., "Genetic Transformation of Murine Bone Marrow Cells to Methotrexate Resistance," *Blood,* 62(1):180–185 (1983).

Cepko, C., "Retrovirus Vectors and Their Applications in Neurobiology," *Neuron,* 1:345–353 (1988).

Chada et al., "Cross–Reactive Lysis of Human Targets Infected with Prototypic and Clinical Human Immunodeficiency Virus Type 1 (HIV–1) Strains by Murine Anti–HIV–1 IIIB env–Specific Cytotoxic T Lymphocytes," *J. Virol.,* 67(6):3409–3417 (1993).

Chakrabarti et al., "Expression of the HTLV–III Envelope Gene by a Recombinant Vaccinia Virus," *Nature,* 320:535–537 (1986).

Chan et al., "Mammalian Saccoma–Leukemia Viruses. I. Infection of Feline, Bovine, and Human Cell Cultures With Snyder–Theilen Feline Sarcoma Virus," *J. Nat'l Cancer Inst.,* 52(2):473–481 (1974).

Cline et al., "Gene Transfer in Intact Animals," *Nature,* 284:422–425 (1980).

Collins et al., "Transfer of Functional EGF Receptors to an IL3–Dependent Cell Line," *J. Cell. Physiology,* 137:292–298 (1988).

Cone et al., "High–Efficiency Gene Transfer Into Mammalian Cells: Generation of Helper–Free Recombinant Retrovirus with Broad Mammalian Host Range," *Proc. Nat'l Acad. Sci. USA,* 81:6349–6353 (1984).

Cone et al., "HLA–DR Gene Expression in a Proliferating Human Thyroid Cell Clone (12S)" *Endocrinology,* 123(4):2067–2074 (1988).

Cortes et al., "Successful Immunotherapy in a Murine Metastasizing Fibrosarcoma Model," *J. Surg. Onco.,* 25:289–295 (1984).

Crowley et al., "Generation of Human Antologous Melanoma–specific Cytotoxic T–Cells Using HLA–A2–matched Allogeneic Melanomas," *Cancer Research,* 50:492–498 (1990).

Culliton, B.J., "Designing Cells to Deliver Drugs," *Science(News & Comment),* 246:746–751 (1989).

Dadaglio et al., "Enhancement of HIV–specific Cytotoxic T Lymphocytes Responses by Zidovudine (AZT) Treatment," *Clin. Ex. Immunol.,* 87:7–14 (1992).

Dallo et al., "Humoral Immune Response Elicited by Highly Attenuated Variants of Vaccinia Virus and by an Attenuated Recombinant Expressing HIV–1 Envelope Protein," *Virology,* 173:323–329 (1989).

De Baetselier et al., "Differential Expression of H–2 Gene Products in Tumour Cells is Associated with Their Metastatogenic Properties," *Nature,* 288:179–181 (Nov. 13, 1980).

Deen et al., "A Soluble Form of CD4 (T4) Protein Inhibits AIDS Virus Infection," *Nature,* 331:82–84 (Jan. 7, 1988).

Doherty et al., "Recombinant Vaccinia Viruses and The Development of Immunization Strategies Using Influenza Virus," *J. Inf. Diseases,* 159(6):1119–1122 (Jun., 1989).

Donner et al.,, "McDonough Feline Sarcoma Virus: Characterization of the Molecularly Cloned Provirus and Its Feline Oncogene (v–fms)," *J. Virol,* 41(2):489–500 (1982).

Earl et al., "Biological and Immunological Properties of Human Immunodeficiency Virus Type 1 Envelope Glycoprotein: Analysis of Proteins with Truncations and Deletions Expressed by Recombinant Vaccinia Viruses," *J. Virology,* 65(1):31–41 (1991).

Ellrodt et al., "The Hidden Dangers of AIDS Vaccination," *Nature,* 325:765 (1987).

Embretson et al., "Pseudotyped Retroviral Vectors Reveal Restrictions to Reticuloendotheliosis Virus Replication in Rat Cells," *J. Virology,* 60(2):662–668 (1986).

Episkopou et al., "Cell–specificed Expression of a Selectable Hybrid Gene," *Proc. Nat'l Acad. Sci., USA,* 81:4657–4661 (1984).

Estin et al., "Recombinant Vaccinia Virus Vaccine Against the Human Melanoma Antigen p97 for Use in Immunotherapy," *Proc. Nat'l Acad. Sci., USA,* 85:1052–1056 (1988).

Evans et al., "An Engineered Poliovirus Chimaera Elicits Broadly Reactive HIV–1 Neutralizing Antibodies," *Nature,* 339:385–388 (1989).

Faraji–Shadan et al., "A Putative Approach for Gene Therapy Against Human Immunodeficiency Virus (HIV)," *Medical Hypothesis,* 32:81–84 (1990).

Fauci et al., "Development and Evaluation of a Vaccine for Human Immunodeficiency Virus (HIV) Infection," *Ann. Intern. Med.,* 110(5):373–385 (1989).

Fisher–Hoch et al., "Protection of Rhesus Monkeys From Fatal Lassa Fever by Vaccination With a Recombinant Vaccinia Virus Containing the Lassa Virus Glycoprotein," *Proc. Nat'l Acad. Sci., USA,* 86:317–321 (1989).

Flexner et al., "Characterization of Human Immunodeficiency Virus gag/pol Gene Products Expressed by Recombinant Vaccinia Viruses," *Virology,* 166:339–349 (1988).

Fox, J.L., "No Winners Against AIDS," *Bio/Technology,* 12:128 (1994).

Friedmann, T., "Progress Toward Human Gene Therapy," *Science,* 244:1275–1281 (1989).

Friedmann, T., "The Future For Gene–Therapy—A Reevaluation," *Ann. N.Y. Acad. Sci.,* 265:141–152 (1975).

Gansbacher et al., "Retroviral Vector–mediated Gamma–Interferon Gene Transfer into Tumor Cells Generated Potent and Long Lasting Antitumor Immunity," *Cancer Research,* 50:7820–7825 (1990).

Gattoni–Celli et al., "Partial Suppression of Anchorage-–Independent Growth and Tumorigenicity in Immunodeficient Mice by Transfection of the H–2 Class I Gene H–2L$^d$ into a Human Colon Cancer Cell Line (HCT)," *Proc. Nat'l Acad. Sci., USA,* 85:8543–8547 (1988).

Gilboa, E., "Retroviral Gene Transfer: Applications to Human Therapy," Memorial Sloan–Kettering Cancer Center, Program in Molecular Biology, New York, New York, *Prog. Clin. Biol. Res., USA,* 352:301–311 (1990).

Gilboa et al., "Gene Therapy for Infectious Diseases: the AIDS Model," *Trends in Genetics,* 10(4):139–144 (Apr., 1994).

Greenough et al., "Normal Immune Function and Inability to Isolate Virus in Culture in an Individual with Long–Term Human Immunodeficiency Virus Type 1 Infection," *AIDS Res. And Human Retrovir.,* 10(4):395–403 (1994).

Gruber et al., "Retroviral Vector–Mediated Gene Transfer into Human Hematopoietic Progenitor Cells," *Science,* 230:1057–1061 (1985).

Guarini et al., "In Vitro Differentiation and Antigenic Changes in Human Melanoma Cell Lines," *Cancer Immunol. Immunother.,* 30:262–268 (1989).

Hatzoglou et al., "Hormonal Regulation of Chimeric Genes Containing the Phosphoenolpyruvate Carboxykinase Promoter Regulatory Region in Hepatoma Cells Infected by Murine Retroviruses," *J. Biol. Chem.,* 263(33):17798–17808 (1988).

Hellerman et al., "Secretion of Human Parathyroid Hormone From Rat Pituitary Cells Infected With a Recombinant Retrovirus Encoding Preproparathyroid Hormone," *Pro. Nat'l Acad. Sci., USA,* 81:5340–5344 (1984).

Hester et al., "Differential Expression of Class I Major Histocompatibility Complex Determinants by Lymphoblastic Leukemia–Lymphoma Cell lines," *J. Nat. Cancer Inst.,* 82:1209–1214 (1990).

Hoffenbach et al., "Unusually High Frequencies of HIV–Specific Cytotoxic T Lymphocytes in Humans," *J. Immunol.,* 142:452–462 (1989).

Holt et al., "Inducible Production of c–fos Antisense RNA Inhibits 3T3 Cell Proliferation," *Proc. Nat'l Acad. Sci., USA,* 83:4794–4798 (1986).

Holzman, D., "FDA Team Recommends Phase III Trials for AIDS Vaccine," *Genetic Engineering News,* 15(15): 1 & 21 (1995).

Howell et al., "Gene Therapy for Thioguanine–resistant Human Leukemia," *Mol. Biol. Med.,* 4:157–168 (1987).

Hu et al., "Effect of Immunization with a Vaccinia–HIV env Recombinant on HIV Infection of Chimpanzees," *Nature,* 328:721–723 (1987).

Hu et al., "Processing, Assembly, and Immunogenicity of Human Immunodeficiency Virus Core Antigens Expressed by Recombinant Vaccinia Virus," *Virology,* 179:321–329 (1990).

Hunt et al., "Retrovirus–Expressed Hemagglutinin Protects against Lethal Influenza Virus Infections," *J. Virology,* 62:3014–3019 (1988).

Hussey et al., "A Soluble CD4 Protein Selectively Inhibits HIV Replication and Synytium Formation," *Nature,* 331:78–81 (1988).

Irwin et al., "Direct Injection of a Recombinant Retroviral Vector Induces Human Immunodeficiency Virus–Specific Immune Responses in Mice and Nonhuman Primates," *J. Virol.,* 68(8):5036–5044 (1994).

Isobe et al., "Induction of Antitumor Immunity in Mice by Allo–Major Histocompatibility Complex I Gene Transfectant With Strong Antigen Expression," *J. Nat. Cancer Inst.,* 81:1823–1828 (1989).

Izant and Weintraub, "Constitutive and Conditional Suppression of Exogenous and Endogenous Genes by Anti–Sense RNA," *Science,* 229:345–352 (1985).

Jaroff, L., "Giant Step for Gene Therapy," *Time,* Medicine, pp. 74–76 (Sep. 24, 1990).

Jolly et al., "Induction of Anti–HIV–1 Immune Responses by Retroviral Vectors," *Biotechnology Therapeutics,* 2(12):179–193 (1990–1991).

Joly et al., "Cell–Mediated Suppression of HIV–Specific Cytotoxic T Lymphocytes," *J. Immunol.,* 143(7):2193–2201 (1989).

Joyner et al., "Construction and Transfer of Recombinant Retrovirus Clones Carrying the HSV–1 Thymidine Kinase Gene," *The Ontario Cancer Institute, Department of Medical Biophysics, University of Toronto, Toronto, Canada, Developmental Biology Using Purified Genes,* pp. 535–546 (1981).

Joyner et al., "Retrovirus Transfer of a Bacterial Gene Into Mouse Hematopoietic Progenitor Cells,"0 *Nature,* 305:556–558 (1983).

Kantoff et al., "Expression of Human Adenosine Deaminase in Nonhuman Primates After Retrovirus–Mediated Gene Transfer," *J. Exp. Med.,* 166:219–234 (1987).

Kasid et al., "Human Gene Transfer; Characterization of Human Tumor–Infiltrating Lymphocytes as Vehicles for Retroviral–Mediated Gene Transfer in Man," *Proc. Nat'l Acad. Sci., USA,* 87:473–477 (1990).

Kast et al., "Eradication of Adenovirus E1–Induced Tumors by E1A–Specific Cytotoxic T Lymphocytes," *Cell,* 59:603–614 (1989).

Katoh et al., "Inhibition of Retroviral Protease Activity by an Aspartyl Proteinase Inhibitor," *Nature,* 329(6140):654–656 (Oct. 15–21, 1987).

Keller et al., "Expression of a Foreign Gene in Myeloid and Lymphoid Cells Derived From Multipotent Haematopoietic Precursors," *Nature,* 318:149–154 (1985).

Klavinskis et al., "Molecularly Engineered Vaccine Which Expresses an Immunodominant T–Cell Epitope Induces Cytotoxic T Lymphocytes That Confer Protection from Lethal Virus Infection," *J. Virol.*, 63(10):4311–4316 (1989).

Koenig et al., "Mapping the Fine Specificity of a Cytolytic T Cell Response to HIV–1 nef Protein," *J. Immunol.*, 145:127–135 (1990).

Kohn et al., "Retroviral–Mediated Gene Transfer into Mammalian Cells," *Blood Cells*, 13:285–298 (1987).

Korman et al., "Expression of Human Class II Major Histocompatibility Complex Antigens Using Retrovirus Vectors," *Proc. Nat'l Acad. Sci.*, *USA*, 84:2150–2154 (1987).

Koup et al., "Shutting Down HIV," *Nature*, 370:416 (1994).

Koup et al., "Temporal Association of Cellular Immune Responses with the Initial Control of Viremia in Primary Human Immunodeficiency Virus Type 1 Syndrome," *J. Virol.*, 68(7):4650–4655 (1994).

Kourilsky and Claverie, "MHC–Antigen Interaction: What Does the T Cell Receptor See?," *Adv. In Immunol.*, 45:107–193 (1989).

Lang et al., "Expression of a Hemopoietic Growth Factor cDNA in a Factor–Dependent Cell Line Results in Autonomous Growth and Tumorigenicity," *Cell*, 43(2 Pt 1):531–541 (Dec., 1985).

Lathe et al., "Tumour Prevention and Rejection With Recombinant Vaccinia," *Nature*, 326:878–880 (Apr. 30, 1987).

Ledley, F.D., "Somatic Gene Therapy for Human Disease: Background and Prospects (Part I)," *J. Pediatrics*, 110(1):1–8 (Jan., 1987).

Lee et al., "Gene Therapy: Clipping the Wings of Nature's Own Gene Transfer Vectors," *Can. Med. Assoc. J.*, 134:311–313 (Feb. 15, 1986).

Levy, J.A., "Pathogenesis of Human Immunodeficiency Virus Infection," *Microbiological Reviews*, 57(1):183–289 (1993).

Lewis, R., "Gene Transfer Methods Evolve as Technology Moves Potential Products Toward the Market," *Genetic Engineering News*, 15(7):1, 17 & 25 (1995).

Lieberman et al., "Immunotherapy with Antologous Expanded, HIV–Specific Cytotoxic T Cells in Infected Patients with CD4 Counts Between 100–400/MM$^3$," *J. Cell Biochem. (Suppl.)* 18B:163 (*Abstract J516*) (1994).

Linial et al., "An Avian Oncovirus Mutant (SE 21Q1b) Deficient in Genomic RNA: Biological and Biochemical Characterization," *Cell*, 15:1371–1381 (1978).

Linial, M., "Transfer of Defective Avian Tumor Virus Genomes by a Rous Sarcoma Virus RNA Packaging Mutant," *J. Virology*, 38(1):380–382 (Apr., 1981).

Lotteau et al., "Modulation of HLA Class II Antigen Expression by Transfection of Sense and Antisense DRα cDNA," *J. Exp. Med.*, 169:351–356 (1989).

Lotze et al., "Recent Advances ihn Cellular Immunology: Implication for Immunity to Cancer," *Immunology*, 11:190–193 (1990).

Luytjes et al., "Amplification, Expression, and Packing of a Foreign Gene by Influenza Virus," *Cell*, 59:1107–1113 (1989).

Mariman, E.C.M., "New Strategies For AIDS Therapy and Prophylaxis," *Nature*, 318:414 (1985).

Mason et al., "The Hypogonadal Mouse: Reproductive Functions Restored by Gene Therapy," *Science*, 234:1372–1378 (1986).

McAleer et al., "Human Hepatitis B Vaccine from Recombinant Yeast," *Nature* 307:178–180 (1984).

McCormick, D., "Human Gene Therapy: The First Round," *Biotechnology*, 3(8):689–693 (1985).

McCune et al., "Endoproteolytic Cleavage of gp160 Is Required for the Activation of Human Immunodeficiency Virus," *Cell*, 53:55–67 (1988).

McCune et al., "Renal Cell Carcinoma Treated by Vaccines For Active Specific Immunotherapy: Correlation of Survival with Skin Testing by Autologous Tumor Cells," *Cancer Immunol. Immunother.*, 32:62–66 (1990).

McMichael et al., "Cytotoxic T–Cell Immunity to Influenza," *The New England J. Med.*, 309:13–17 (1983).

Mercola et al., "Insertion of a New Gene of Viral Origin into Bone Marrow Cells of Mice," *Science*, 208:1033–1035 (1980).

Merz, B., "Gene Therapy May Have Future Role in Cancer Treatment," *JAMA*, 257:150–151 (1987).

Michel et al., "HIV–Specific T Lymphocyte Immunity in Mice Immunized with a Recombinant Vaccinia Virus," *Eur. J. Immunol.*, 18:1917–1924 (1988).

Miedema et al., "Maintenance of High Level Cytotoxic T–Cell (CTL) Response in Long–Term Survivors of HIV Infection," *J. Cell. Biochem., Suppl. 17D*:75 (*Abstract N350*) (1993).

Miller, A.D., "Retrovirus Packaging Cells," *Human Gene Therapy*, 1:5–14 (1990).

Miller et al., "Expression of a Retrovirus Encoding Human HPRT in Mice," *Science*, 225:630–632 (1984).

Miller et al., "Generation of Helper–Free Amphotropic Retroviruses That Transduce a Dominant–Acting, Methotrexate–Resistant Dihydrofolate Reductase Gene," *Mol. And Cell. Biol.*, 5(3):431–437 (1985).

Miller et al., "A Transmissible Retrovirus Expressing Human Hypoxanthine Phosphoribosyltransferase (HPRT): Gene Transfer into Cells Obtained From Humans Deficient in HPRT," *Proc. Nat'l Acad. Sci., USA*, 80:4709–4713 (1983).

Morgan et al., "Expression of an Exogenous Growth Hormone Gene by Transplantable Human Epidermal Cells," *Science*, 237:1476–1479 (1987).

Morrow, J.F., "The Prospects for Gene Therapy in Humans," *Ann. N.Y. Acad. Sci.*, 265:13–21 (1975).

Mosier et al., "Resistance to Human Immunodeficiency Virus 1 Infection of SCID Mice Reconstituted With Peripheral Blood Leukocytes from Donors Vaccinated With Vaccinia gp160 and Recombinant gp160," *Proc. Nat'l Acad. Sci., USA*, 90;2443–2447 (1993).

Mulligan, R.C., "Construction of Highly Transmissible Mammalian Cloning Vehicles Derived from Murine Retroviruses," *Experimental Manipulation of Gene Expression*, 8:155–173 (1983).

Nabel et al., "Recombinant Gene Expression in Vivo Within Endothelial Cells of the Arterial Wall," *Science*, 244:1342–1344 (1989).

Newell et al., "Herpes Simplex Virus–Induced Stromal Keratitis: Role of T–Lymphocyte Subsets in Immunopathology," *J. Virol.*, 63(2):769–775 (1989).

Nixon et al., "HIV–1 gag–Specific Cytotoxic T Lymphocytes Defined with Recombinant Vaccinia Virus and Synthetic Peptides," *Nature*, 336:484–487 (1988).

Overell et al., "Stably Transmitted Triple–Promoter Retroviral Vectors and Their Use in Transformation of Primary Mammalian Cells," *Mol. And Cell. Biol.*, 8:1803–1808 (1988).

Palmer et al., "Genetically Modified Skin Fibroblasts Persist Long After Transplantation but Gradually Inactive Introduced Genes," *Proc. Nat'l Acad. Sci., USA*, 88:1330–1334 (1991).

Panicali et al., "Construction of Live Vaccines by Using Genetically Engineered Poxviruses: Biological activity of Recombinant Vaccinia Virus Expressing Influenza Virus Hemagglutinin," *Proc. Nat'l Acad. Sci., USA*, 80:5364–5368 (1983).

Pantaleo et al., "Major Expansion of CD8+ T Cells With a Predominant vβ Usage During the Primary Immune Respone to HIV," *Nature*, 370:463–467 (1994).

Parkerson III et al., "Immunotherapy With Viral Specific Cytotoxic T Lymphocytes in HIV–1 Infection," *Workshop on HIV/SIV Pathogenesis and Mucosal Transmission and AIDS Postdoctoral Fellows Meeting*, p. 52 (*Abstract for Poster 51*) (1994).

Plata et al., "AIDS Virus–Specific Cytotoxic T Lymphocytes in Lung Disorders," *Nature*, 328:348–351 (1987).

Quinnan, Jr. et al., "Cytotoxic T Cells in Cytomegalovirus Infection: HLA–Restricted T–Lymphocyte and Non–T–Lymphocyte Cytotoxic Responses Correlate with Recovery from Cytomegalovirus Infection in Bone–Marrow–Transplant Recipients," *New Eng. J. Med.*, 307:7–13 (1982).

Redfield et al., "A Phase I Evaluation of the Safety and Immunogenicity of Vaccination with Recombinant gp160 in Patients with Early Human Immunodeficiency Virus Infection," *The New England J. Med.*, 324:1677–1684 (1991).

Reif, A.E., "Vaccination of Adult and Newborn Mice of a Resistant Strain (C57BL/6J) against Challenge with Leukemias Induced by Moloney Murine Leukemia Virus," *Cancer Research*, 45:25–31 (1985).

Reimann et al., "Introduction of a Selectable gene Into Murine T–Lymphoblasts by a Retroviral Vector," *J. Immunol. Methods*, 89:93–101 (1986).

Rein et al., "Myristylation Site in Pr65$^{gag}$ is Essential for Virus Particle Formation by Moloney Murine Leukemia Virus," *Proc. Nat'l Acad. Sci., USA*, 83:7246–7250 (Oct., 1986).

Rosenberg et al., "Gene Transfer into Humans–Immunotherapy of Patients with Advanced Melanoma, Using Tumor–Infiltrating Lymphocytes Modified by Retroviral Gene Transduction," *The New England J. Med.*, 323:570–578 (1990).

Rosenfeld et al., "Adenovirus–Mediated Transfer of a Recombinant α1–Antitrypsin Gene to the Lung Epithelium in Vivo," *Science*, 252:431–434 (1991).

Rota et al., "Comparison of Inactivated, Live and Recombinant DNA Vaccines Against Influenza Virus in a Mouse Model," *Virus Research*, 16:83–93 (1990).

Rouse et al., "Antiviral Cytotoxic T Lymphocyte Induction and Vaccination," *Rev. Infect. Dis.*, 10:16–33 (1988).

Rubenstein et al., "Construction of a Retrovirus Capable of Transducing and Expressing Genes in Multipotential Embryonic Cells," *Proc. Nat'l Acad. Sci., USA*, 81:7137–7140 (1984).

Ruprecht et al., "Vaccination with a Live Retrovirus: The Nature of the Protective Immune Response," *Proc. Nat'l Acad. Sci., USA*, 87:5558–5562 (1990).

Ruscetti et al., "Three Independent Isolates of Feline Sarcoma Virus Code for Three Distinct gag–x Polyproteins," *J. Virol.*, 35(1):259–264 (1980).

Sabin et al., "History of Sabin Attenuated Poliovirus Oral Live Vaccine Strains," *J. Biol. Standardization*, 1:115–118 (1973).

Safrit et al., "Characterization of Human Immunodeficiency Virus Type 1–Specific Cytotoxic T Lymphocyte Clones Isolated During Acute Seroconversion: Recognition of Autologous Virus Sequences with a Conserved Immunodominant Epitope," *J. Exp. Med.*, 179:463–472 (1994).

Saito et al., "The Generation and Selection of the T Cell Repertoire: Insights from Studies of the Molecular Basis of T Cell Recognition," *Immunological Reviews*, 101:81–193 (1988).

Salk, J., "Prospects for the Control of AIDS by Immunizing Seropositive Individuals," *Nature*, 327:473–476 (1987).

Shimotohno et al., "Formation of Infectious Progeny Virus after Insertion of Herpes Simplex Thymidine Kinase Gene into DNA of an Avian Retrovirus," *Cell*, 26:67–77 (1981).

Shinitzky and Skornick, "Cancer Immunotherapy With Autologous and Allogeneic Vaccines: A Practical Overview," *EORTC Genitourinary Group Monograph Basic Research and Treatment of Renal Cell Carcinoma Metastasis*, 9:95–125 (1990).

Siu et al., "Isolation of the Murine Intercellular Adhesion Molecule 1(ICAM–1) Gene: ICAM–1 Enhances Antigen—Specific T Cell Activation," *J. Immunology*, 143:3813–3820 (1989).

Sleckman et al., "Expression and Function of CD4 in a Murine T–Cell Hybridoma," *Nature*, 328:351–353 (Jul. 23, 1987).

Smith et al., "Loss of HLA–A,B,C Allele Products and Lymphocyte Function–Associated Antigen 3 in Colorectal Neoplasia," *Proc. Nat'l Acad. Sci., USA*, 86:5557–5561 (1989).

St. Louis et al., "An Alternative Approach to Somatic Cell Gene Therapy," *Proc. Nat'l Acad. Sci., USA*, 85:3150–3154 (1988).

Stover et al., "New Use of BCG for Recombinant Vaccines," *Nature*, 351:456–460 (1991).

Strair et al., "Recombinant Retroviruses Encoding Cell Surface Antigens as Selectable Markers," *J. Virology*, 62(12):4756–4759 (1988).

Stratowa et al., "Recombinant Retroviral DNA Yielding High Expression of Hepatitis B Surface Antigen," *EMBO J.*, 1(12):1573–1578 (1982).

Strebel et al., "The HIV 'A' (sor) Gene Product is Essential for Virus Infectivity," *Nature*, 328:728–730 (1987).

Stuhlmann et al., "Introduction of a Selectable Gene into Different Animal Tissue by a Retrovirus Recombinant Vector," *Proc. Nat'l Acad. Sci.,*, 81:7151–7155 (1984).

Sutter et al., "Cytotoxic Immune Response of Puppies to Feline Sarcoma Virus Induced Tumors," *Veterinary Immunology and Immunopathology*, 7:131–138 (1984).

Tabin et al., "Adaptation of a Retrovirus as a Eucaryotic Vector Transmitting the Herpes Simplex Virus Thymidine Kinase Gene," *Mol Cell. Biol.*, 2(4):426–436 (1982).

Takahashi et al., "A Single Amino Acid Interchange Yields Reciprocal CTL Specificities for HIV–1 gp160," *Science*, 246:118–121 (1989).

Takahashi et al., "An Immunodominant Epitope of the Human Immunodeficiency Virus Envelope Glycoprotein gp160 Recognized by Class I Major Histocompatibility Complex Molecule–Restricted Murine Cytotoxic T Lymphocytes," *Proc. Nat'l Acad. Sci., USA*, 85:3105–3109 (1988).

Tellier et al., "New Strategies for AIDS Therapy and Prophylaxis," *Nature*, 318:414 (1985).

Temin, H.M., "Retrovirus Vectors: Promise and Reality," *Science*, 246:983 (1989).

Thomason and Booth, "Stable Incorporation of Bacterial Gene into Adult Rat Skeletal Muscle in Vivo," *Amer. J. Physiology,* 258:C578–C581 (1990).

Torpey, III et al., "Effects of Adoptive Immunotherapy with Autologous CD8+ T Lymphocytes on Immunologic Parameters: Lymphocytes Subsets and Cytotoxic Activity," *Clinical Immunol. Immunopath.,* 68(5):263–272 (1993).

Townsend et al., "Cytotoxic T Cells Recognize Fragments of the Influenza Nucleoprotein," *Cell,* 42:457–467 (1985).

Traversari et al., "Expression of Retrovirus–Related, Cytotoxic T Lymphocyte–and Transplantation–Defined Antigens in NIH/3T3 Transfectants After a Single Passage in Nude Mice," *J. Immunol.,* 142:2887–2894 (1989).

Van Den Eynde et al., "Presence on a Human Melanoma of Multiple antigens Recognized by Autologous CTL," *Int. J. Cancer,* 44:634–640 (1989).

Verma, I.M., "Gene Therapy," *Scientific American,* 262:68–72 & 81–84 (1990).

Voss et al., "Potential Significance of the Cellular Immune Response against the Macaque Strain of Simian Immunodeficiency Virus ($SIV_{MAC}$) in Immunized and Infected Rhesus Macaques," *J. Gen. Virol.,* 73:2273–2281 (1992).

Wachsman et al., "HTLV $_X$ Gene Mutants Exhibit Novel Transcriptional Regulatory Phenotypes," *Science,* 235:674–677 (Feb. 6, 1987).

Walker et al., "HIV–1 Reverse Transcriptase Is a Target for Cytotoxic T Lymphocytes in Infected Individuals," *Science,* 240:64–66 (1988).

Walker et al., "HIV–specific Cytotoxic T Lymphocytes in Seropositive Individuals," *Nature,* 328:345–348 (1987).

Wallich et al., "Abrogation of Metastatic Properties of Tumor cells by de novo Expression of H–2K Antigens Following *H–2 Gene Transfection,*" *Nature,* 315:301–305 (1985).

Warner et al., "Induction of HIV–specific CTL and Antibody Responses in Mice Using Retroviral Vector–Transduced Cells," *AIDS Res. And Human Retrovir.,* 7(8):645–655 (1991).

Watanabe et al., "Construction of a Helper Cell Line for Avian Reticuloendotheliosis Virus Cloning Vectors," *Mol. And Cell. Biol.,* 3(12):2241–2249 (1983).

Watanabe et al., "Encapsidation Sequences for Spleen Necrosis Virus, An Avian Retrovirus, are, Between the 5' Long Terminal Repeat and the Start of the gag Gene," *Proc. Nat'l Acad. Sci., USA,* 79:5986–5990 (1982).

Wathen et al., "Immunization of Cotton Rats with the Human Respiratory Syncytial Virus F Glycoprotein Produced Using a Baculovirus Vector," *J. Infect. Disease,* 159(2):255–264 (Feb., 1989).

Weber and Jay, "MHC Class I Gene Expression by Tumors: Immunotherapeutic Implications," *Curr. Top. Microbiol. Immunol.,* 137:140–147 (1988).

Weber et al., "Immunotherapy of a Murine Tumor with Interleukin 2," *J. Exp. Med.,* 166:1716–1733 (1987).

Wei et al., "Construction and Insolation of a Transmissible Retrovirus Containing the src Gene of Harvey Murine Sarcoma Virus and The Thymidine Kinase Gene of Herpes Simplex Virus Type 1," *J. Virology,* 39(3):935–944 (1981).

Weis et al., "Eukaryotic Chromosome Transfer: Linkage of the Murine Major Histocompatibility Complex to an Inserted Dominant Selectable Marker," *Proc. Nat'l Acad. Sci., USA,* 81:4879–4883 (1984).

Weis et al., "H–2L$^d$ Antigen Encoded by a Recombinant Retrovirus Genome Is Expressed on the Surface of Infected Cells," *Mol. & Cell. Biol.,* 5(6):1379–1384 (1985).

Wilson et al., "Correction of CD18–Deficient Lymphocytes by Retrovirus–Mediated Gene Transfer," *Science,* 248:1413–1416 (1990).

Wilson et al., "Implantation of Vascular Grafts Lined with Genetically Modified Endothelial Cells," *Science,* 244:1344–1346 (1989).

Wolff et al., "Grafting Fibroblasts Genetically Modified to Produce L–dopa in a Rat Model of Parkinson Disease," *Proc. Nat'l Acad. Sci., USA,* 86:9011–9014 (1989).

Wong et al., "Retroviral Transfer and Expression of the Interleukin–3 Gene in Hemopoietic Cells," *Genes Dev.,* 1:358–365 (1987).

Xu et al., "Factors Affecting Long–Term Stability of Moloney Murine Leukemia Virus–Based Vectors," *Virology,* 171:331–341 (1989).

Yap et al., "Transfer of Specific Cytotoxic T Lymphocytes Protects Mice Inoculated with Influenza Virus," *Nature,* 273:238–239 (1978).

Yasutomi et al., "Simian Immunodeficiency Virus–Specific CD8+Lymphocyte Response in Acutely Infected Rhesus Monkeys," *J. Virol.,* 67(3):1707–1711 (1993).

Zagury et al., "Immunization Against AIDS in Humans," *Nature,* 326:249–250 (1987).

Zarling et al., "Proliferative and Cytotoxic T Cells to AIDS Virus Glycoproteins in Chimpanzees Immunized with a Recombinant Vaccinia Virus Expressing AIDS Virus Envelope Glycoproteins," *J. Immunol.,* 139:988–990 (1987).

Zarling et al., "T–Cell Responses to Human AIDS Virus in Macaques Immunized with Recombinant Vaccinia Viruses," *Nature,* 323:344–346 (1986).

Zarling et al., "Herpes Simplex Virus (HSV)–Specific Proliferative and Cytotoxic T–Cell Responses in Human Immunized with an HSV Type 2 Glycoprotein Subunit Vaccine," *J. Virol.,* 62(12):4481–4485 (Dec., 1988).

Zbar et al., "Tumor Rejection Mediated by an Amphotrophic Murine Leukemia Virus," *Cancer Research,* 43:46–53 (1983).

Zinkernagel et al., "Antiviral Protection By Virus–Immune Cytotoxic T Cells: Infected Target Cells Are Lysed Before Infectious Virus Progeny Is Assembled," *J. Exp. Med.,* 145:644–651 (1977).

Zwiebel et al., "Drug Delivery by Genetically Engineered Cell Implants," *Ann. N.Y. Acad. Sci.,* 618:394–404 (1990).

Verma et al., "Expression and Regulation of Rat Growth Hormone Gene in Mouse Fibroblasts," *In: Eukaryotic Viral Vectors,* Gluzman, Y, (ed.), Cold Spring Harbor Laboratory, pp. 159–164 (1982).

Czarniecki et al., "Synergistic Antiviral and Antiproliferative Activities of *Escherichia coli*–Derived Human Alpha, Beta, and Gamma Interferons," *J. Virology,* 49(2):490–496 (1984).

Davison et al., "The Complete DNA Sequence of Varicella–Zoster Virus," *J. Gen. Virol.,* 67:1759–1816 (1986).

Maniatis et al., "Regulation of Inducible and Tissue–Specific Gene Expression," *Science,* 236:1237–1245 (Jun. 5, 1987).

Temin, H.M., "Retrovirus Vectors For Gene Transfer: Efficient Integration Into and Expression of Exogenous DNA in Vertebrate Cell Genomes," *In: Gene Transfer,* Kucherlapati, R., (ed.), Plenum Press, New york, pp. 149–187 (1986).

Field et al., "Isolation and Characterization of Acyclovir––resistant Mutants of Herpes Simplex Virus," *J. General Virology,* 49:115–124 (1980).

Besnard et al., "Selection Against Expression of the *Escherichia coli* Gene gpt in hprt+Mouse Teratocarcinoma and Hybrid cells," *Mol. Cell. Biol.,* 7(11):4139–4141 (1987).

Borrelli et al., "Targeting of an Inducible Toxic Phenotype in Animal Cells," *Proc. Nat'l Acad. Sci.,* 85:7572–7576 (1988).

Toohey et al., "Multiple Hormone–Inducible Enhancers as Mediators of Differential Transcription," *Mol. Cell. Biol.,* 6(12):4526–4538 (1986).

Schrewe et al. "Cloning of the Complete Gene for Carcinoembryonic Antigen: Analysis of Its Promoter Indicates a Region Conveying Cell Type–Specific Expression," *Mol. Cell. Biol.,* 10(6):2738–2748 (1990).

Doppler et al., "Prolactin and Glucocorticoid Hormones Synergistically Induce Expression of Transfixed Rat β–Casein Gene Promoter Constructs in a Mammary Epithelial Cell Line," *Proc. Nat'l Acad. Sci.,* 86:104–108 (1989).

Mullen et al., "Transfer of the Bacterial Gene for Cytosine Deaminase to Mammalian Cell Confers Lethal Sensitivity to 5–Fluorocytosine: A Negative Selection System," *Proc. Nat'l Acad. Sci., USA,* 89:33–37 (1992).

Searle et al., "The Potential of Carboxypeptidase $G_2$–Antibody Conjugates as Anti–Tumour Agents. I. Preparation of Antihuman Chorionic Gonadotropin–Carboxypeptidase $G_2$ and Cytotoxicity of the Conjugate Against JAR Choriocarcinoma Cells in Vitro," *Brit. J. Can.,* 263(33):17798–17808 (1988).

Deng et al., "The Mouse Thymidylate Synthase Promoter: Essential Elements Are in Close Proximity to the Transcriptional Initiation Sites," *Mol. Cell. Biol.,* 9(9):4079–4082 (1989).

Rosen et al., "Intragenic Cis–Acting art Gene–Responsive Sequences of the Human Immunodeficiency Virus," *Proc. Nat'l Acad. Sci., USA,*85:2071–2075 (1988).

Irvin, "Purification and Partical Characterization of the Antiviral Protein from *Phytolacca americana* Which Inhibits Eukaryotic Protein Synthesis," *Archives of Biochemistry and Biophysics,* 169:522–528 (1975).

Mulligan et al., "Synthesis of Rabbit β–Globulin in Cultured Monkey Kindney Cells Following Infection with a SV40 β–Globulin Recombinant Genome," *Nature,* 277:108–114 (1979).

Irvin et al., Purification and Properties of a Second Antiviral Protein from *Phytolacca americana* Which Inactivates Eukaryotic Ribosomes: *Archives of Biochemistry and Biophysics,* 200(2):418–425 (1980).

Stripe et al., "Gelonin, a New Inhibitor of Protein Synthesis, Nontoxic to Intact Cells," *J. Biol. Chem.,* 255(14):6947–6953 (1980).

Parnes et al., "Mouse $β^2$–Microglobulin cDNA Clones: A Screening Procedure for cDNA Clones Corresponding to Rare mRNAs," *Proc. Nat'l Acad. Sci., USA,*78(4):2253–2257 (1981).

Barbieri et al., "Purification and Partial Characterization of Another Form of the Antiviral Protein From the Seeds of *Phytolacca americana* L. (Pokeweed)," *Biochem. J.,* 203:55–59 (1982).

Ball et al., "Monoclonal Antibodies to Myeloid Differentiation Antigens: In Vivo Studies of Three Patients With Acute Myelogenous Leukemia," *Blood,* 62(6):1203–1210 (1983).

Mekalanos et al., "Cholera Toxin Genes: Nucleotide Sequence, Deletion Analysis and Vaccine Development," *Nature,* 306:551–557 (1983).

Dubensky et al., "Direct Transfection of Viral and Plasmid DNA into the Liver or Spleen of Mice," *Proc. Nat'l Acad. Sci., USA,* 891:7529–7533 (1984).

Stanton et al., "Nucleotide Sequence Comparison of Normal and Translocated Murine c–myc Genes," *Nature,* 310:423–425 (1984).

Eglitis et al., "Gene Expression in Mice After High Efficiency Retroviral–Mediated Gene Transfer," *Science,* 230:1395–1398 (1985).

Coussens et al., "Tyrosine Kinase Receptor with Extensive Homology to EGF Receptor Shares Chromosomal Location with neu Oncogene," *Science,* 230:1138–1139 (1985).

Lamb et al., "Nucleotide Sequence of Cloned cDNA Coding for Preproricin," *Eur. J. Biochem.,* 148:265–270 (1985).

Tweten et al., "Diptheria Toxin—Effect of Substituting Aspartic Acid for Glutamic Acid 148 on ADP Ribosyltransferase Activity," *J. Biol. Chem.,* 260:10392–10394 (1985).

Rosenberg et al., "Observations on the Systemic Administration of Autologous Lymphokine–Activated Killer Cells and Recombinant Interleukin–2 to Patients with Metastatic Cancer," *New Eng. J. Med.,* 313(23):1485–1492 (1985).

Furman et al., "Phosphorylation of 3'–azido–3'deoxythymidine and Selective Interaction of the 5'–trisphosphate with Human Immunodeficiency Virus Reverse Transcriptase," *Proc. Nat'l Acad. Sci., USA,* 83:8333–8337 (1987).

Lifson et al., "AIDS Retrovirus Induced Cytopathology: Giant Cell Formation and Involvement of CD4 Antigen," *Science,* 232:1123–1127 (1986).

Lifson et al., "Role od Envelope Glycoprotein Carbohydrate in Human Immunodeficiency virus (HIV) Infectivity and Virus–Induced Cell Fusion," *J. Exper. Med.,* 164:2101–2106 (1986).

McDougal et al., "Binding of HTLV–III/LAV to T4+T Cells by a Complex of the 110K Viral Protein and the T4 Molecule," *Science,* 231:382–385 (1986).

Pert et al., "Octapeptides Deduced from the Neuropeptide Receptor–like Pattern of Antigen T4 in Brain patently Inhibit Human Immunodeficiency Virus Receptor Binding and T–Cell Infectivity," *Proc. Nat'l Acad. Sci., USA,* 83:9254–9258 (1986).

To et al., "Inhibition of Retroviral Replication by Anti–Sense RNA," *Mol. Cell. Biol.,* 6:4758–4762 (1986).

Goodbourn et al., "The Human β–Interferon Gene Enhancer Is Under Negative Control," *Cell,* 45:601–610 (1986).

Krissansen et al., "Chromosomal Locations of the Gene Coding for the CD3 (T3) Gamma Subunit of the Human and Mouse CD3/T–Cell Antigen Receptor Complexes," *Immunogenetics,* 26:258–266 (1987).

Wang and Huang, "pH–Sensitive Immunoliposomes Mediate Target–Cell–Specific Delivery and Controlled Expression of a Foreign Gene in Mouse," *Proc. Nat'l Acad. Sci., USA, L*84:7851–7855 (1987).

Jackson et al., "Nucleotide Sequence Analysis of the Structural Genes for Shiga–like Toxin I Encoded by Bacteriophage 900J from *Escherichia coli,"* *Microbial Pathogenesis,* 2:147–153 (1987).

Maher, III and Dolnick, "Specific Hybridization Arrest of Dihydrofolate Reductase mRNA in Vitro Using Anti–Sense RNA or Anti–Sense Oligonucleotides," *Archives of Biochemistry and Biophysics,* 253(1):214–220 (1987).

Carroll and Collier, "Active Site of *Pseudomonas aeruginosa* Exotoxin A," *J. Biol. Chem.,* 262(18):8707–8711 (1987).

Bzik et al., "Molecular Cloning and Sequence Analysis of the *Plasmodium falciparum* Dihyrofolate Reductase–Thymidylate Synthase Gene," *Proc. Nat'l Acad. Sci., USA,* 84:8360–8364 (1987).

Calderwood et al., "Nucleotide Sequence of the Shiga–like Toxin Genes of *Escherichia coli,*" *Proc. Nat'l Acad. Sci., USA,* 84:4364–4368 (1987).

Wallner et al., "Primary Structure of Lymphocyte Function–Associated Antigen 3 (LFA–3): The Ligand of the T Lymphocyte CD2 Glycoprotein," *J. Exper. Med.,* 166:923–932 (1987).

Tal et al., "Human HER2 (neu) Promotor: Evidence for Multiple Mechanisms for Transcriptional Initiation," *Mol. Cell. Biol.,* 7(7):2597–2601 (1987).

Dillman, "Antibody Therapy," *Principles of Cancer Biotherapy,* Chapter 13, pp. 395–432 (1987).

Mendelson et al., "Expression and Rescue of a Nonselected Marker from an Integrated AA Vector," *Virology,* 166:154–165 (1988).

Simmons et al., "ICAM, an Adhesion Ligand of LFA–1, is Homologous to the Neural Cell Adhesion Molecule NCAM" *Nature,* 331:624–627 (1988).

Bodner et al., "The Pituitary–Specific Transcription Factor GHF–1 Is a Homeobox–Containing Protein," *Cell,* 55:505–518 (1988).

Ingraham et al., "A Tissue–Specific Transcription Factor Containing a Homeodomain Specifies a Pituitary Phenotype," *Cell,* 55:519–529 (1988).

Anderson et al., "A Conserved Sequence in the T–Cell Receptor β–Chain Promoter Region, " *Proc. Nat'l Acad. Sci., USA,* 85:3551–3554 (1988).

Ohlsson et al., "A Beta–Cell–Specific Protein Binds to the Two Major Regulatory Sequences of the Isulin Gene Enhancer," *Proc. Nat'l Acad. Sci., USA,* 85:4228–4231 (1988).

Moss and Flexner, "Vaccinia Virus Expression Vectors," *Annals of the N.Y. Academy of Sciences,* 569:86–103 (1989).

Kit, "Recombinant–derived Modified–live Herpesvirus Vaccines," *Adv. Exp. Med. Biol.,* 251:219–236 (1989).

Samulski et al., "Helper–Free Stocks of Recombinant Adeno–Associated Viruses: Normal Integration Does Not Require Viral Gene Expression," *J. Virology,* 63(9):3822–3828 (1989).

Wu et al., "Targeting Genes: Delivery and Persistent Expression of a Foreign Gene Driven by Mammalian Regulatory Elements in Vivo," *J. Biol. Chem.,* 264(29):16985–16987 (1989).

Xiong et al., "Sindbis Virus: An Efficient, Broad Host Range Vector for Gene Expression in Animal Cells," *Science,* 243:1188–1191 (1989).

Sanchez and Holmegren, "Recombinant System for Overexpression of Cholera Toxin B Subunit in *Vibrio cholerae* as a Basis for Vaccine Development," *Proc. Nat'l Acad. Sci., USA,* 86:481–485 (1989).

Swift et al., "Differential Requirements for Cell–Specific Elastase I Enhancer Domains in Transfected Cells and Transgenic Mice," *Genes & Development,* 3:687–696 (1989).

Benvenisty et al., "Separate Cis–Regulatory Elements Confer Expression of Phophoenolpyruvate Carboxykinase (GTP) Gene in Different Cell Lines," *Proc. Nat'l Acad. Sci., USA,* 89:1118–1122 (1989).

Fan and Maniatis, "Two Different Virus–Inducible Elements are Required for Human β–Interferon Gene Regulation," *EMBO J.,* 8(1):101–110 (1989).

Winoto and Baltimore, "A Novel, Inducible and T Cell–Specific Enhancer Located at the 3' End of the T Cell Receptor α Locus," *EMBO J.,* 8(3):729–733 (1989).

Camper and Tilghman, "Postnatal Repression of the α–Fetoprotein Gene is Enhancer Independent," *Genes & Development,* 3:537–546 (1989).

Karlsson et al., "Individual Protein–Binding Domains of the Isulin Gene Enhancer Positively Activate β–Cell–Specific Transcription," *Mol. Cell. Biol.,* 9:823–827 (1989).

Baldwin and Burden, "Muscle–Specific Gene Expression Controlled by a Regulatory Element Lacking a MyoD1–Binding Site," *Nature,* 347:716–720 (1989).

McDonnell et al., "Reconstitution of the Vitamin D–Responsive Osteocalcin Transcription Unit in *Saccharomyces cerevisiae,*" *Mol. Cell. Biol.,* 9:3517–3523 (1989).

Van Assendelft et al., "The β–Globin Dominant Control Region Activates Homologous and Heterologous Promoters in a Tissue–Specific Manner," *Cell,* 56:969–977 (1989).

Feuerman et al., "Tissue–Specific Transcription of the Mouse α–Fetoprotein Gene Promoter Is Dependent on HFN–1," *Mol. Cell. Biol.,* 9:4204–4212 (1989).

Vaulont et al., "Analysis by Cell–Free Transcription of the Liver–Specific Pyruvate Kinase Gene Promoter," *Mol. Cell. Biol.,* 9:4409–4415 (1989).

Kerner et al., "Sequence Elements in the Human Osteocalcin Gene Confer Basal Activation and Inducible Response to Hormanal Vitamin $D_3$, " *Proc. Nat'l Acad. Sci., USA,* 86:4455–4459 (1989).

Gross and Merrill, "Thymidine Kinase Synthesis is Repressed in Nonreplicating Muscle Cells a Translational Mechanism that Does not Affect the Polysomal Distribution of Thymidine Kinase mRNA," *Proc. Nat'l Acad. sci., USA,* 86:4987–4991 (1989).

Tussey and Felder, "Tissue–Specific Genetic Variation in the Level of Mouse Alcohol Dehydrogenase is Controlled Transcriptionally in Kidney and Posttranscriptionally in Liver," *Proc. Nat'l Acad. Sci., USA,* 86:5903–5907 (1989).

Forrester et al., "Molecular Analysis of the Human β–Globin Locus Activation Region," *Proc. Nat'l Acad. Sci., USA,* 86:5439–5443 (1989).

Flexner et al., "Attenuation and Immunogenicity in Primates of Vaccinia Virus Recombinants Expressing Human Interleukin–2," *Vaccine,* 8:17–21 (1990).

Collins et al., "Primary Amino Acid Sequence of α–Trichosanthin and Molecular Models for Abrin A–Chain and α–Trichosanthin," *J. Biol. Chem.,* 265(15):8665–8669 (1990).

Kerr et al., "Antibody–Penicillin–V–Amidase Conjugates Kill Antigen–Positive Tumor Cells When Combined With Doxorubicin Pheonoxyacetamide," *Cancer Immunol. Immunother.,* 31:202–206 (1990).

Markose et al., "Vitamin D–Mediated Modifications in Protein–DNA Interactions at Two Promoter Elements of the Osteoclacin Gene," *Proc. Nat'l Acad. Sci., USA,* 87:1701–1705 (1990).

Acsadi et al., "Human Dystrophin Expression in mdx Mice After Intramuscular Injection of DNA Constructs," *Nature,* 352:815–818 (1991).

Williams et al., "Introduction of Foreign Genes into Tissues of Living Mice by DNA–Coated Microprojectiles," *Proc. Nat'l Acad. Sci.,* 88:2726–2730 (1991).

Wood et al., "Preproabrin: Genomic Cloning, Characterization and the Expression of the A–Chain in *Escherichia coli,*" *European Journal of Biochemistry,* 266(11):6848–6852 (1991).

Evensen et al., "Direct Molecular Cloning and Expression of Two Distinct Abrin A–Chain," *J. Biol. Chem.*, 266(11):6848–6852 (1991).

Curiel et al., "High–Efficiency Gene Transfer Mediated by Adenovirus Coupled to DNA–Polylysine Complexes," *Human Gene Therapy*, 3:147–154 (1992).

Rabinovitz, "The Pleiotypic Response to Amino Acid Deprivation is the Result of Interactions Between Component of the Glycolysis and protein Synthesis," *FEBS*, 302(2):113–116 (1992).

Vrudhula et al., "Prodrugs of Doxorubicin and Melphalan and Their Activation by a Monoclonal Antibody–Penicillin–G Amidase Conjugate," *J. Med. Chem.*, 36:9149–923 (1993).

Adam et al., "Identification of a Signal in a Murine Retrovirus That Is Sufficient for Packaging of Nonretroviral RNA into Virions", *J. Virology*, 62:3802 (1988).

Baltimore, "Intracellular Immunization", *Nature*, 335:395 (1988).

Cepko et al., "Construction and Applications of a Highly Transmissible Murine Retrovirus Shuttle Vector", *Cell*, 37:1053 (1984).

Cone et al., "Regulated Expression of a Complete Human β–Globin Gene Encoded by a Transmissible Retrovirus Vector", *Mol. Cell. Biol.*, 7:887 (1987).

Danos et al., "Safe and efficient generation of recombinant retroviruses with amphotropic and ecotropic host ranges", *PNAS (USA)*, 85:6460 (1988).

Dayton et al., "The Trans–Activator Gene of the Human T Cell Lymphotropic Virus Type III Is Required for Replication" *Cell*, 44:941 (1986).

Dzierzak et al., "Lineage–Specific Expression Of A Human β–Globin Gene In Murine Bone Marrow Transplant Recipients Reconstituted With Retrovirus–Transduced Stem Cells", *Nature*, 331:35 (1988).

Felber et al., "A Quantitative Bioassay For HIV–1 Based On Trans–Activation", *Science*, 239:184 (1988).

Felgner et al., "Lipofection: A highly efficient, lipid–mediated DNA–transfection procedure", *PNAS (USA)*, 84:7413 (1987).

Frankel et al., "Dimerization of the tat protein from human immunodeficiency virus: A cysteine–rich peptide mimics the normal metal–linked dimer interface", *PNAS (USA)*, 85:6297 (1988).

Frankel et al., "Tat Protein From Human Immunodeficiency Virus Forms A Metal–Linked Dimer", *Science*, 240:70 (1988).

Friedman et al., "Expression Of A Truncated Viral Trans–Activator Selectively Impedes Lytic Infection By Its Cognate Virus", *Nature*, 335:452 (1988).

Furman et al.,"Inhibition of Herpes Simlex Virus–Induced DNA Polymerase Activity and Viral DNA Replication by 9–(2–Hydroxyethoxymethyl)guanine and Its Triphosphate", *J. Virology*, 32:72 (1979).

Ganz et al., "Natural Peptide Antibiotics of Human Neutrophils", *J. Clin. Invest.*, 76:1427 (1985).

Goelz, Hypomethylation of DNA from Benign and Malignant Human Colon Neoplasms, *Science*, 228:187 (1985).

Graham et al., "A New Technique for the Assay of infectivity of Human Adenovirus 5 DNA", *Virology*, 52:456 (1973).

Guild et al., "Development of Retrovirus Vectors Useful for Expressing Genes in Cultured Murine Embryonal Cells and Hematopoietic Cells In Vivo", *J. Virol.*, 62:3795 (1988).

Hirsch, "Aids Commentary: Azidothymidine", *J. Infect. Dis.*, 157:427 (1988).

Ho et al., "A T–cell–specific transcriptional enhancer element 3' fo $C_\alpha$ in the human T–cell receptor α locus", *PNAS (USA)*, 86:6714 (1989).

Kantoff et al., "Correction of adenosine deaminase deficiency in cultured human T and B cells by retrovirus–mediated gene transfer", *PNAS (USA)*, 83:6563 (1986).

Kriegler et al., "Transformation Mediated by the SV40 T Antigens: Separation of the Overlapping SV40 Early Genes with a Retroviral Vector", *Cell*, 38:483 (1984).

Malim et al., "The HIV–1 rev trans–activator acts through a structured target sequence to activate nuclear export of unspliced viral mRNA", *Nature*, 338:254 (1989).

Maniatis et al., *Molecular Cloning: A Laboratory Manual*, Cold Spring Harbor Press, 1982, pp. 22–26.

Mansour et al., "Disruption Of The Proto–Oncogene int–2 In Mouse Embryo–Derived Stem Cells: A General Strategy For Targeting Mutations To Non–Selectable Genes", *Nature*, 336:348 (1988).

Miller et al., "Redesign Of Retrovirus Packaging Cell Lines To Avoid Recombination Leading To Helper Virus Production", *Mol. Cell. Biol.*, 6:2895 (1986).

Mitsuya et al., "Strategies For Antiviral Therapy In AIDS", *Nature*, 325:773 (1987).

Muesing et al., "Regulation of mRNA Accumulation by a Human Immunodeficiency Virus Trans–Activator Protein", *Cell*, 48:691 (1987).

Nabel et al., "Alternative Mechanisms for Activation of Human Immunodeficiency Virus Enhancer in T Cells", *Science*, 239:1299 (1988).

Overhauser et al., "Generation of Gluococorticoid–Responsive Moloney Murine Leukemia Virus by Inseration of Regulatory Sequences for Murine Mammary Tumor Virus into the Long Terminal Repeat", *J. Virol.*, 54:133 (1985).

Palmiter et al., "Cell Lineage Abiation In Transgenic Mice By Cell–Specific Expression Of A Toxin Gene", *Cell*, 50:435 (1987).

Peterlin et al. "Elevated levels of mRNA can account for the trans–activation of human immunodeficiency virus", *PNAS (USA)*, 83:9734 (1986).

Phelps et al., "The Human Papillomavirus Type 16 E7 Gene Encodes Transactivation and Transformation Functions Similar to Thos of Adenovirus E1A", *Cell*, 53:539 (1988).

Selsted et al., "Primary Structures of Three Human Neutrophil Defensins", *J. Clin. Invest.*, 76:1436 (1985).

Shinnick et al., "Nucleotide sequence of Moloney murine leukaemia virus", *Nature*, 293:543 (1981).

Smith et al., "Blocking of HIV–1 Infectivity by a Soluble, Secreted Form of the CD4 Antigen", *Science*, 238:1704 (1987).

Sodroski et al., "Trans–acting Transcriptional Regulation of Human T–cell Leukemia Virus Type III Long Terminal Repeat", *Science*, 227:171 (1985).

Sodroski et al., "Location Of The Trans–Activating Region On The Genome Of Human T–Cell Lymphotropic Virus Type III", *Science*, 229:74 (1985).

Treisman, "Identification of a Protein–Binding Site That Mediates Transcriptional Response of the C–fos Gene to Serum Factors", *Cell*, 46:567 (1986).

Van Beveran et al., "Nucleotide Sequence of the Genome of a Murine Sarcoma Virus", *Cell*, 27:91 (1981).

Walbot et al., "Plant development and ribozymes for pathogens", *Nature*, 334:196 (1988).

Wasmoen et al., "Biochemical and Amino Acid Sequence Analysis of Human Eosinophil Granule Major Basic Protein", *J. Biol. Chem.*, 263:12559 (1988).

Yee et al., "Gene Expression From Transcriptionally Disabled Retroviral Vectors", *PNAS (USA)*, 84:5197 (1987).

Yu et al., "Self–inactivating retroviral vectors designed for transfer of whole genes into mammalian cells", *PNAS (USA)*, 83:3194 (1986).

Piatak et al J. Biol. Chemistry 263:4837–4843 (1988).

D. Cournoyer et al. (1993) Ann. Rev. Immunol 11:297–329.

W. F. Anderson (1992) Science 256:808–813.

M. I Johnston et al. (1993) Science 260:1286–1293.

B. F. Haynes (1993) Science 260:1279–1286.

F. L. Moolten (1987) Med. Hypothesis 24:43–51.

F. L. Moolten (1986) Cancer Research 46:5276–5281.

Maxwell et al., Cancer Research 46:4660–4664 (1986).

"Report and Recommendations of the Panel to Assess the NIH Investment in Research on Gene Therapy," Orkin and Motulsky, Co–chairs, Dec. 7, 1995.

Sodroski et al., Science 227:171–173 (1985).

Pierce et al., *Proc. Natl. Acad. Sci.* (1988) 85:1482–1486.

Patarca et al., *Proc. Natl. Acad. Sci.* (1988) 85:2733–2737.

METHODS AND POLYNUCLEOTIDE CONSTRUCTS FOR TREATING HOST CELLS FOR INFECTION OR HYPERPROLIFERATIVE DISORDERS

RELATED APPLICATION

This application is a continuation of application Ser. No. 07/461,461, filed Jan. 17, 1990, now abandoned, which is a CIP of Ser. No. 07/300,637 filed Jan. 23, 1989 now abandoned.

TECHNICAL FIELD

This invention relates to genetic engineering and the treatment of hyperproliferative disorders and infection.

BACKGROUND OF THE INVENTION

The therapy of viral infection is in its infancy. Bacterial infection is typically treated with agents, such as antibiotics, which take advantage of the differences in metabolism between the infecting organism and its host. However, viruses largely employ the host's own enzymes to effect their replication, and thus leave few opportunities for pharmacological intervention. By employing strong regulatory elements, the virus obtains transcription and translation of its own genes at the expense of host genes.

In mammals, viral infection is combatted naturally by cytotoxic T-lymphocytes, which recognize viral proteins when expressed on the surface of host cells, and lyse the infected cells. Destruction of the infected cell prevents the further replication of virus. Other defenses include the expression of interferon, which inhibits protein synthesis and viral budding, and expression of antibodies, which remove free viral particles from body fluids. However, induction of these natural mechanisms require exposure of the viral proteins to the immune system. Many viruses, for example herpes simplex virus-1 (HSV-1), exhibit a dormant or latent phase, during which little or no protein synthesis is conducted. The viral infection is essentially invisible to the immune system during such phases.

Retroviruses carry the infectious form of their genome in the form of a strand of RNA. Upon infection, the RNA genome is reverse-transcribed into DNA, and is typically then integrated into the host's chromosomal DNA at a random site. On occasion, integration occurs at a site which truncates a gene encoding an essential cellular receptor or growth factor, or which places such a gene under control of the strong viral cis-acting regulatory element, which may result in transformation of the cell into a malignant state.

Viruses may also be oncogenic due to the action of their trans-acting regulatory factors on host cell regulatory sequences. In fact, oncogenesis was the characteristic which lead to the discovery of the first known retroviruses to infect humans. HTLV-I and HTLV-II (human T-lymphotropic viruses I and II) were identified in the blood cells of patients suffering from adult T-cell leukemia (ATL), and are believed to induce neoplastic transformation by the action of their trans activating factors on lymphocyte promoter regions. HTLV-I and II preferentially infect human lymphocytes, and on occasion, cause their transformation into malignancy. Since then, two additional retroviruses have been found to infect humans: HIV-I and HIV-II, the etiological agents of AIDS. However, HIV-I and II apparently contribute to cancer only through their immunosuppressive effects.

HIV I and II apparently infect cells which express the CD4 surface protein. This protein is present in abundance on thymocytes and some T-lymphocytes, and to a lesser extent, on some antigen-presenting cells. HIV infection is initially characterized by flu-like symptoms, followed by a long latency period, which may last five to ten years. Upon entering its active phase, HIV infection results in a rapid decline in the population of "helper" T-lymphocytes (TH), which is usually recognized as a decline in the ratio of $T4^+/T8^+$ ($CD4^+/CD8^+$) T-lymphocytes. The patient typically experiences severe diarrhea, and if the central nervous system is infected, exhibits a form of dementia. The depletion of $T_H$ cells cripples the immune system, and the patient succumbs to an opportunistic infection by, for example $P.$ $carinii$ or cytomegalovirus, or to Karposi's sarcoma. The natural immune system appears wholly incapable of combatting HIV infection, despite the typical presence of apparently neutralizing serum antibody titers during latency.

Current therapy for HIV infection per se is limited mainly to administration of AZT to inhibit viral progression, although M. S. Hirsch, $J$ $Infect$ $Dis$ (1988) 157:427–31 reported synergistic inhibition of HIV by AZT with GM-CSF (granulocyte-monocyte colony stimulating factor) or α interferon. AZT (3'-azido-3'-deoxythymidine) is representative of a class of dideoxynucleoside (ddN) antiviral agents. These agents rely on the ability of host DNA polymerases to reject a ddN, and the tendency of viral polymerases to accept ddNs and incorporate them into replicating polynucleotides. Upon incorporation, a ddN stops polymerization, as it lacks the 3' hydroxyl group necessary for the next phosphodiester linkage. The ddNs are typically inactive in their administered form, and depend on phosphorylation by host cell enzymes for conversion to the active triphosphate ddNTP.

H. Mitsuya et al, $Nature$ (1987) 325:773–78 disclosed the organization of the HIV genome, and suggested various strategies for development of HIV therapies. Speculated therapies included administration of antisense RNA (as free strands or encoded by an "antivirus") to inhibit viral transcription, administration of glycosylation inhibitors, administration of interferons to inhibit viral budding, and administration of dideoxynucleoside analogues to inhibit viral replication. Dideoxynucleoside analog drugs useful for HIV therapy (e.g., AZT, ddC, etc.) depend on host cell enzymes for activation by phosphorylation. D. Baltimore, $Nature$ (1988) 335:395–96 suggested treating AIDS by removing bone marrow cells from an infected subject, and transfecting hematopoietic cells in the bone marrow extract with DNA or virus encoding an RNA or protein able to interfere with HIV growth. The DNA could encode RNA that might bind to HIV regulatory proteins, antisense RNA, mutant viral polypeptides, or a viral DNA-binding protein lacking its regulator function. The transfected cells would then be re-introduced into the subject, and provided with a selective advantage to insure dissemination.

A. I. Dayton et al, $Cell$ (1986) 44:941–47 disclosed that the HIV tat gene is essential for viral protein synthesis and replication. Dayton suggested that one might inhibit HIV by interference with tat, without otherwise affecting the host cell. M. A. Muesing et al, $Cell$ (1987) 48:691–701 disclosed that the tat protein (rather than tat mRNA alone) is essential for transactivation. Muesing also found that a tat-art fusion (having 114 amino acids fused to the C-terminus of tat by deletion of 7 nucleotides) retained full tat activity. A. D. Frankel et al, $Science$ (1988) 240:70–73 disclosed that tat forms metal-linked dimers in vitro, and suggested that possible treatments for AIDS may involve chelation of metal ions, or competition for tat monomer binding. A. D. Frankel et al, $Proc$ $Nat$ $Acad$ $Sci$ $USA$ (1988) 85:6297–30 disclosed the synthesis of an HIV-1 tat fragment which retains the metal-binding properties of tat. The fragment formed heterodimers with native tat, and can displace tat in homodimers. Frankel suggested using the tat fragment to inhibit tat dimerization, using liposomes to deliver the peptides or a tat-fragment gene. The amino acid sequence reported for tat from one HIV-1 isolate is

| Met | Glu | Pro | Val | Asp | Pro | Arg | Leu | Glu | Pro |
|---|---|---|---|---|---|---|---|---|---|
| Trp | Lys | His | Pro | Gly | Ser | Gln | Pro | Lys | Thr |
| Ala | Cys | Thr | Asn | Cys | Tyr | Cys | Lys | Lys | Cys |
| Cys | Phe | His | Cys | Gln | Val | Cys | Phe | Ile | Thr |
| Lys | Ala | Leu | Gly | Ile | Ser | Tyr | Gly | Arg | Lys |
| Lys | Arg | Arg | Gln | Arg | Arg | Arg | Pro | Pro | Gln |
| Gly | Ser | Gln | Thr | His | Gln | Val | Ser | Leu | Ser |
| Lys | Gln | Pro | Thr | Ser | Gln | Ser | Arg | Gly | Asp |
| Pro | Thr | Gly | Pro | Lys | Glu. | | | | |

A similar protein is found in HIV-2.

The tar sequence, which acts in cis and is regulated by HIV tat, is found approximately at nucleotides +19 to +82 in the HIV-1 genome. The sequence contains two extended, inverted repeats, and is thus predicted to be able to form stem loop structures (Muessing, supra). HIV-2 exhibits a similar region.

Haseltine, U.S. Pat. No. 4,738,922 disclosed the HTLV I and II LTR promoter regions, and their use with transactivators (luk) in vectors for amplified expression of heterologous proteins, exemplified by chloramphenicol acetyltransferase (CAT). HTLV-I LTR apparently promotes constitutive expression, which is further amplified in the presence of HTLV-I luk, while HTLV-II LTR apparently requires HTLV-II luk for expression. Haseltine mentioned that viral trans-acting factors can alter the expression of host cell genes as well as viral genes, and Haseltine disclosed the concept of inserting a vector having the HTLV LTR fused to a heterologous gene into a cell having the HTLV genome, which results in the trans-activation of the heterologous gene and the overexpression of its product. Haseltine disclosed the use of the HTLV LTR in the absence of luk to generate empty capsid vaccines, and suggested using the HTLV LTR for expression of antigens, to provide for destruction of the cell by monoclonal or polyclonal antibodies.

E. A. Dzierzak et al, *Nature* (1988) 331:35–41 disclosed a prototypical gene therapy method in mice. Dzierzak removed bone marrow cells from mice, exposed the mice to lethal radiation, and introduced human β-globin (BG) genes into the removed marrow using a retroviral vector, pSV(X) neo. The BG gene was inserted to read in the opposite direction from proviral transcription, and constructs both with and without the viral LTR enhancer regions were prepared. The mice were then reconstituted with the recombinant bone marrow, containing hematopoietic stem cells. Dzierzak found that human β-globin was expressed in the resulting recombinant mice, and that the expression was found only in cells of erythroid lineage. J-K Yee et al, *Proc Nat Acad Sci USA* (1987) 84:5197–201 disclosed construction of retroviral vectors encoding HPRT under control of either the metallothionein promoter or the human cytomegalovirus (hCMV) promoter. Yee found that HPRT expression doubled when transcriptional regulatory sequences were deleted from the U3 region of the retroviral LTR.

S.-F. Yu et al, *Proc Nat Acad Sci USA* (1986) 83:3194–98 disclosed the construction of self-inactivating ("SIN") retroviral gene transfer vectors. SIN vectors are created by deleting the promoter and enhancer sequences from the U3 region of the 3' LTR. A functional U3 region in the 5' LTR permits expression of the recombinant viral genome in appropriate packaging cell lines. However, upon expression of its genomic RNA and reverse transcription into cDNA, the U3 region of the 5' LTR of the original provirus is deleted, and is replaced with the U3 region of the 3' LTR. Thus, when the SIN vector integrates, the non-functional 3' LTR U3 region replaces the functional 5' LTR U3 region, and renders the virus incapable of expressing the full-length genomic transcript. Yu constructed a recombinant virus using the Mo-MuLV LTR regions and packaging (psi) sequence, and inserted a neomycin resistance (Neo) gene under control of either a metallothionein promoter (virus MT-N), an HSV tk promoter (virus TK-N), or a SV40 promoter (virus SV-N) as a selectable marker. Yu also inserted a human c-fos gene under control of a human metallothionein promoter (hMT) into TK-N, and demonstrated inducible transcription of c-fos in NIH 3T3 cells after infection with the recombinant virus.

S. L. Mansour et al, *Nature* (1988) 336:348–52 disclosed a method for selecting cells after homologous recombination with a linear transfecting vector. A linear vector was prepared having a region homologous to a target gene, a neomycin resistance gene inserted in an exon of the homologous region, and an HSV-tk gene outside the homologous region. Upon specific homologous recombination, the transformed cell displays a phenotype negative for the target region and HSV-tk, and positive for neomycin resistance (homologous recombination into the target site disrupts the target site gene, and fails to incorporate the tk gene). The phenotype distinguishes cells having homologous recombination from non-specific integration, as the latter cells will display a phenotype positive for the target gene, HSV-tk, and neomycin resistance. Neomycin resistance is tested by culturing cells in neomycin, while $tk^+$ is tested by culturing cells in gancyclovir (which is converted to a toxic product by tk).

R. D. Palmiter et al, *Cell* (1987) 80:435–43 disclosed the preparation of transgenic mice having a DNA construct encoding the diphtheria A chain under control of the elastase promoter. The elastase promoter is active only in pancreatic acinar cells, and promotes the expression of elastase. The DNA constructs were microinjected into mouse eggs, and the resulting progeny examined. Transgenic mice in which the construct was active failed to develop normal pancreatic tissue.

M. E. Selsted et al, *J Clin Invest* (1985) 76:1436–39 disclosed the primary amino acid sequence for three related human cytotoxic effector polypeptides, termed human neutrophil antimicrobial peptides (HNPs). The three HNPs have 29–30 amino acid residues and exhibit activity against bacteria, fungi, and herpes simplex virus (T. Gantz et al, *J Clin Invest* (1985) 76:1427–35).

T. L. Wasmoen et al, *J Biol Chem* (1988) 263:12559–63 disclosed the primary amino acid sequence of human eosinophil granule major basic protein (MBP). MBP is an effector polypeptide having 117 amino acid residues, a pI of 10.9, and exhibiting cytotoxic activity against mammalian cells and parasites.

M. A. Adam et al, *J Virol* (1988) 62:3802–06 disclosed retroviral vectors which exhibit efficient RNA packaging, having a psi+sequence. R. D. Cone et al, *Mol Cell Biol* (1987) 7:887–97 disclosed the construction of retroviral vectors (pSVX) including a human β-globin gene, and the use of the recombinant vectors to obtain human β-globin expression in a murine erythroleukemia cell line. A. D. Miller et al, *Mol Cell Biol* (1986) 6:2895–902 disclosed cell lines useful for packaging replication-defective retroviral vectors.

Guild et al, *J Virol* (1988) 62:3795–801 disclosed retroviral vectors using the Mo-MuLV LTRs and psi (packaging) sequence, useful for transfer of entire genes into mammalian cells. Guild employed β-actin and histone promoters (which are active in essentially all cells) to obtain transcription of neo$^r$ (as a selectable marker). Expression of the neo$^r$ was demonstrated in vivo, after virus-infected bone marrow cells were used to reconstitute lethally-irradiated mice.

A. D. Friedman et al, *Nature* (1988) 335:452–54 disclosed transfection of tk$^-$mouse cells with plasmids expressing HSV-1 tk, and HSV-1 VP16. VP16 acts as a trans activator for transcription of the immediate early genes in herpes simplex virus (HSV-1). On the VP16 plasmid, the promoter was replaced with the Mo-MSV promoter, and the carboxy terminal of the VP16 was deleted. The resulting plasmid codes for a mutant VP16 protein which competes with wild type VP16 for DNA binding. Transfected cells exhibited resistance to HSV-1 replication upon later infection. Friedman suggested that one might induce resistance to HIV by transfecting with a dominant mutant of the HIV trans-activator protein (tat).

J. Sodroski et al, *Science* (1985) 229:74–77 disclosed the location of the HIV tat gene. J. Sodroski et al, *Science* (1985) 227:171–73 disclosed construction of a plasmid having CAT under control of the HIV LTR. The HIV LTR contains the transactivating region (tar) gene which is induced by tat. Sodroski discovered that transactivating factors would induce transcription of genes under control of the HIV LTR. B. M. Peterlin et al, *Proc Nat Acad Sci USA* (1986) 83:9734–38 disclosed plasmids having the HIV tar gene, and the effects of orientation and position of tar on transactivation by tat. Peterlin found that tar functions best when downstream from a promoter and an enhancer. Activation with tat increased transcription to RNA. G. J. Nabel et al, *Science* (1988) 239:1299–302 disclosed that a HIV tat-III-CAT fusion plasmid could be activated by HSV and adenovirus trans-acting factors.

B. K. Felber et al, *Science* (1988) 239:184–87 disclosed an assay for HIV, using CD4-expressing cell lines transfected with the chloramphenicol acetyltransferase (CAT) gene under control of the HIV LTR. Upon infection with HIV, the transfected cell lines expressed CAT in proportion to the amount of virus present. Felber suggested using the assay as a means for screening possible anti-HIV drugs for their ability to inhibit viral growth, and for identifying anti-tat drugs.

DISCLOSURE OF THE INVENTION

One aspect of the invention is a method for treating host cells for an infection or a hyperproliferative disorder which is characterized by expression of regulatory factors capable of regulating transcription of DNA, by inserting into the cells a polynucleotide construct having a regulatory region which is activated by the regulatory factor, and an effector gene under control of the regulatory region which renders said cell susceptible to protection or destruction. The gene product may destroy the cell directly, as in the case of cytotoxins, or may increase the cell's susceptibility to destruction by pharmacologic agents. Alternatively, the gene product may directly inhibit the infectious or malignant agent, e.g., by competition for binding sites, by binding as antisense RNA, by expression of protein inhibitors or antibodies, by expression of sequence-specific ribozymes, by expression of enzymes which activate anti-viral compounds, and the like. For example, the activation region may be homologous to the HIV tar region, and the effector gene may encode ricin A or HSV-1 thymidine kinase. Upon infection with HIV, the HIV tat protein activates the tar region, and induces transcription and expression of ricin A, resulting in cell death, or of HSV-1 tk, resulting in cytotoxicity when treated with dideoxynucleoside agents such as gancyclovir.

Another aspect of the invention is a DNA construct which accomplishes the method of the invention.

Another aspect of the invention is a composition useful for delivering the DNA constructs of the invention to host cells.

Another aspect of the invention is a method for protecting specific cell populations within an organism from viral infection, by inserting into the cells of the population a polynucleotide construct comprising a cis-acting sequence which promotes expression of a nearby gene only in the presence of trans-acting factors found substantially only in the selected cell population; and under control of the cis-acting sequence, an effector gene which protects the cell or renders it susceptible to protection. Preferably, the cis-acting sequence is derived from the host. The effector gene is preferably a nucleoside kinase, such as HSV-1 thymidine kinase.

Another aspect of the invention is a polynucleotide construct useful for protecting selected cell populations from infection, which comprises a cis-acting sequence which promotes expression of a nearby gene only in the presence of trans-acting factors found substantially only in the selected cell population; and under control of the cis-acting sequence, an effector gene which protects the cell or renders it susceptible to protection. Preferably, the cis-acting sequence is derived from the host. The effector gene is preferably a nucleoside kinase, such as HSV-1 thymidine kinase.

MODES OF CARRYING OUT THE INVENTION

A. Definitions

Figure 1:
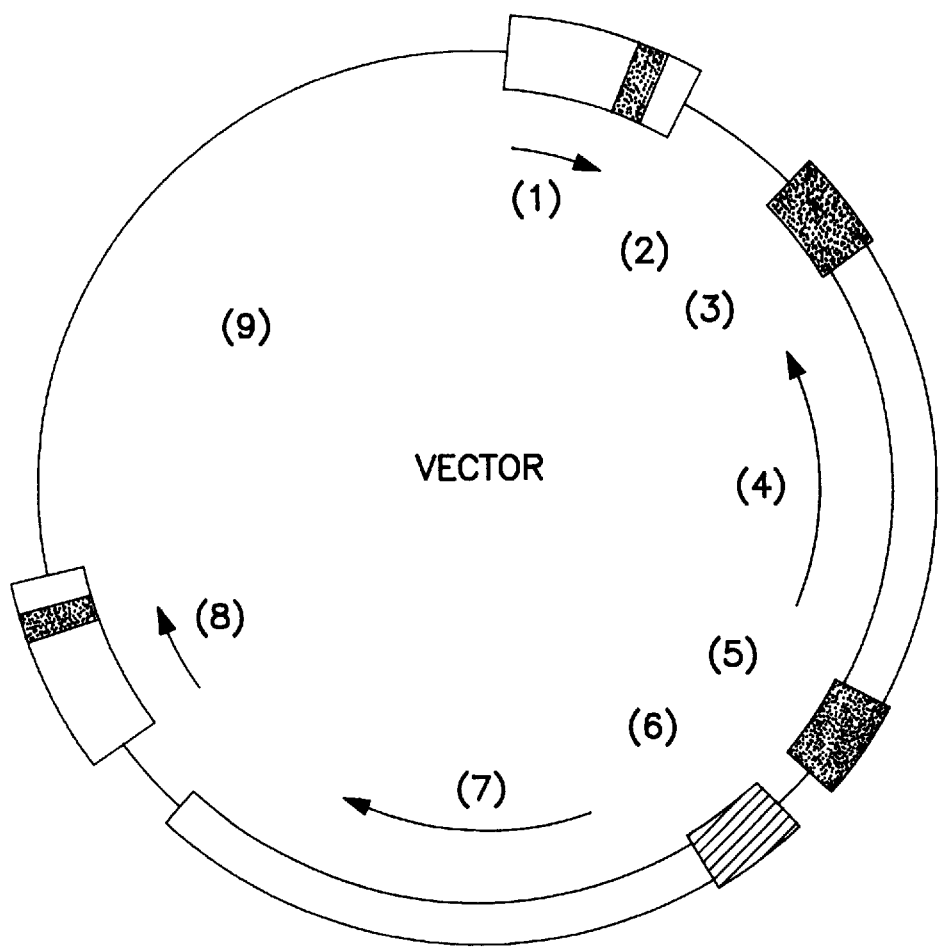
FIG. 1 is a diagram of a generic polynucleotide construct of the invention.

The term "treatment" as used herein refers to reducing or alleviating symptoms in a subject, preventing symptoms from worsening or progressing, inhibition or elimination of the causative agent, or prevention of the infection or disorder in a subject who is free therefrom. Thus, for example, treatment of a cancer patient may be reduction of tumor size, elimination of malignant cells, prevention of metastasis, or the prevention of relapse in a patient who has been cured. Treatment of infection includes destruction of the infecting agent, inhibition of or interference with its growth or maturation, neutralization of its pathological effects, and the like.

The term "infection" as used herein includes infection by viruses, bacteria, fungi, and other parasites, such as leishmania and malarial parasites. "Infectious agents" within the scope of this invention include viruses such as HIV-I, HIV-II, HTLV-I, HTLV-II, herpes simplex virus (HSV), cytomegalovirus (CMV), Epstein-Barr virus (EBV), human papilloma viruses (HPV), hepatitis B virus (HBV), hepatitis C virus (HCV), polio virus, and the like; bacteria such as *B. pertussis*, and the causative agents of tetanus, diphtheria, cholera, and the like; mycobacteria such as *M. tuberculosis*, and the causative agent of leprosy; yeasts and fungi such as *C. albicans* and *P. carinii*; parasites such as malarial Plasmodia, giardia, and the like. Certain methods and constructs of the invention are most suitable for intracellular infectious agents, such as viruses, malaria and the like, while other methods and constructs are applicable to extracellular infections.

The term "hyperproliferative disorder" refers to disorders characterized by an abnormal or pathological proliferation of cells, for example, cancer, psoriasis, hyperplasia and the like.

The term "cis-acting regulatory sequence" refers to a polynucleotide sequence which is capable of responding to a trans-acting factor, and enhancing transcription of cis-located genes. Most appropriate cis-acting regulatory sequences may be derived from the infectious agent they will be used to combat. For example, the tar region of the HIV-1 LTR is a suitable cis-acting regulatory sequence for treatment of HIV-1. Where cell-type specific expression is desired, one may employ cis-acting sequences such as, for example, (for T-cells) the CD2 antigen (Genbank HUMATCCD2), IL-2 (Genbank HUMIL2A), IL-2 receptor (Genbank HUMIL2R1), CD1 antigen (Genbank HUMHTA1), CD3 antigen (Genbank HUMATCT31), CD4 antigen (Genbank HUMATCT4), T-cell protease (Genbank MUSSPTCS); for B-cells, IgG (Genbank HUMIGCA1), MHC-1 antigen (Genbank HUMMHA2); for macrophages, Mac-1 antigen (Genbank HUMLAP), IL-1 (Genbank HUMIL1P), and the like. The cis-acting regulatory sequence may be used in multiple tandem copies, in order to increase its competition with the endogenous cis-acting regulatory site. Suitable sequences for treatment of hyperproliferative disorders (especially cancers) are obtainable from the binding sites of known oncoproteins, or by identification of a known protein whose expression is altered by an oncogene. The cis-acting regulatory sequence must be capable of providing sufficient expression of the effector gene to confer susceptibility to protection or destruction of the cell when activated by the trans-acting factor, without allowing substantial constitutive expression in the absence of the trans-acting factor. The choice of cis-acting sequence will depend upon the trans-acting factor associated with the infection or disorder to be treated, and on the effector gene selected. For example, the HIV LTR contains both the tar region, which is highly selective for HIV tat, and also a region activated by the endogenous nuclear factor NF-κB (the LTR has tandem NF-κB binding regions). Although the tar sequence strongly suppresses expression in the absence of tat (see for example Muesing, Peterlin, supra), the cis-acting elements upstream of the tar sequence influence the degree of constitutive expression ("leakiness") that occurs in the absence of tat. The degree of leakiness in the absence of tat can be controlled by deletion or substitution of the cis-acting elements (e.g., NF-κB binding sites) within the HIV-1 LTR. In order to use the tar sequence with effector genes such as ricin A (which is effective at very low intracellular concentration), one would remove the NF-κB binding sites using restriction endonucleases prior to inserting the vector into host cells. In contrast, if the effector gene encoded a product which was not particularly toxic to the host cell (for example, the rpt-1 protein found in resting T-lymphocytes: see Patarca, supra), but which requires higher concentration for effective viral inhibition, one must employ a cis-acting sequence which provides for strong expression upon induction, but may allow some low-level constitutive expression.

The phrase "susceptible to protection or destruction" means that upon infection or occasion of a hyperproliferative disorder, the presence of the effector gene within the host cell renders the cell either (a) capable of inhibiting the infectious agent or hyperproliferative condition, or (b) the effector gene kills the host cell, or renders it sensitive to an additional exogenous toxic agent. The additional "toxic agent" does not include the host immune system or antibodies, as immunity is often suppressed or ineffective in cases of infection or hyperproliferative disease. Inhibition of infection may be accomplished by reducing intracellular levels of nutrients or metabolites needed by the infectious agent (e.g., purine or pyrimidine nucleotides, carbohydrates, phosphates, etc.), down-regulating host enzymes required by the infectious agent (for example ribosomal enzymes, endogenous proteases, protein folding enzymes, transport proteins, and the like), down-regulating host cell regulatory factors employed by the infectious agent (for example, the NF-κB nuclear factor found in activated lymphocytes which up-regulates HIV-1 transcription), up-regulating viral or host cell factors which suppress viral gene expression, by locking the host cell in a static phase of the mitotic cycle (in the case of certain viruses and hyperproliferative disorders), and the like.

Inhibition may also be accomplished by interference with the infectious agent life cycle, for example by expressing factors which bind to important infectious agent regulatory factors and cause inhibition or deactivation, by expressing host or infectious agent regulatory factors which down-regulate the agent's expression (for example, viruses having a latent phase must have factors which prevent constitutive expression due to their strong regulatory regions), by expressing non-infectious defective mutants of the coat, envelope, or capsid proteins of the infectious agent, by encoding multiple copies of the polynucleotide binding sequence (such that the sequences compete for binding with the infectious agent regulatory agent, and thus limit transcription of the agent), by expression of factors which attack infectious agent proteins, lipids or carbohydrates, (such as neutrophil antimicrobial peptides, eosinophil granule major basic protein, and the like) or which inhibit or prevent processing by infectious agent enzymes. Alternatively, one can encode cytokines which may interfere with or inhibit infectious agents, or which may be cytotoxic, for example, interferons, interleukins, tumor necrosis factors, colony-stimulating factors, transforming growth factors ($\alpha$ and $\beta$), epidermal growth factors, and the like. Cytokine expression is also useful in the treatment of hyperproliferative disorders. For example, cytokines may inhibit or kill tumors directly, or may induce differentiation into a final (non-neoplastic) state. Hyperproliferative disorders may also be treated using any of the other methods noted above which are appropriate. For example, inhibition of cell functions (such as mitotic cycle, protein expression, and the like) can inhibit proliferation.

Cytotoxic techniques may involve the direct expression of a cellular toxin, such as ricin A, diphtheria toxin, and the like, or may employ one of the above-noted methods to a degree which results in cell death (for example, complete inhibition of cellular respiration). Alternatively, one may express an enzyme or protein which renders the cell susceptible to an additional agent, for example, elevated expression of a nucleoside kinase may render the host cell susceptible to the action of gancyclovir or acyclovir, or may increase the potency of an anti-viral agent such as AZT. Dideoxynucleoside analogues (ddNs) such as AZT, dideoxycytidine, acyclovir, gancyclovir, and the like, are relatively non-toxic in their non-phosphorylated form. However, specific viral or intracellular enzymes may convert the ddNs to the corresponding triphosphates, at which point the agent acts as a chain termination agent during transcription or replication. The utility of ddNs is based on the fact that (1) viral polymerases exhibit a higher affinity for ddNs than mammalian polymerases, and (2) some viral nucleoside kinases exhibit a higher rate of phosphorylation for ddNs than mammalian kinases. Thus, viral enzymes (and consequently viral genes) are more affected by chain termination than are mammalian enzymes and genes. The HSV-1 thymidine kinase (HSV-1 tk) is more efficient at converting ddNs to the corresponding triphosphates, thus rendering cells having active HSV-1 tk more susceptible to ddNs.

The term "effector gene" refers to a polynucleotide sequence which, when expressed (due to action by the trans-acting factor on the cis-acting regulatory sequence), renders the host cell susceptible to protection or destruction, as defined above. Cytotoxic proteins within the scope of this invention do not include possibly toxic viral proteins under control of its normal viral regulatory region. The effector gene must be a gene which is not naturally regulated by the cis-acting regulatory region employed. One class of suitable effector genes includes genes encoding a nucleoside kinase capable of phosphorylating dideoxynucleoside analogues at a greater rate than host cell nucleoside kinases, for example HSV-1 thymidine kinase, guanine kinase, plant nucleoside phosphotransferase, *Leishmania donovani* purine 2'-deoxyribonucleosidease, *L. donovani* hypoxanthine-guanine phosphoribosyltransferase, and other suitable enzymes of nucleoside metabolism capable of activating nucleoside antiviral or chemotherapeutic agents. Another class of effector genes includes genes functional at the mRNA level, such as antisense mRNA, and ribozymes (V. Walbot et al, *Nature* (1988) 334:196–97). Another class of effector genes includes genes encoding cytokines useful for antiviral or anti-hyperproliferative disorders, such as tumor necrosis factor, α interferon, β interferon, gamma interferon, transforming growth factor-β, inhibitory peptides, and interleukin-2. Other effector genes within this invention include protease inhibitors, which may inhibit essential protein processing, and inhibitors of glycosylation, phosphorylation, or myristylation of viral proteins. RNase is also suitable. One may alternatively "titrate" the trans-acting factor by providing a plurality of cis-acting sequences in conjunction with a strong termination sequence.

In the context of cell-specific expression, the effector gene must confer susceptibility of the cell to protection, but not destruction. Thus, one avoids deleting an entire class of cells, such as the class of TH cells. This technique can be employed to increase the therapeutic ratio of certain antiviral and chemotherapeutic agents, such as AZT. For example, AZT inhibits HIV replication, but is relatively toxic to bone marrow cells. T-lymphocytes are commonly infected in HIV infection, and are more tolerant of AZT. By transfecting a bone marrow aspirate with a polynucleotide construct which expresses, for example, HSV-1 tk only in T-lymphocytes (for example, under control of the CD4 antigen promoter), reintroducing the cells into the subject, and administering an amount of AZT less than the normal dosage, one can increase the intracellular concentration of phosphorylated AZT in tolerant T-lymphocytes, without increasing the phosphorylated AZT levels in sensitive stem cells (in bone marrow).

Polynucleotide constructs of the invention may also be designed to treat autoimmune disorders, by using a cis-acting sequence which responds to a trans-acting factor characteristic of those specific immune cells which participate in the particular autoimmune disorder treated, and an effector gene which suppresses the activity of those cells.

The term "antisense mRNA" refers to mRNA which is complementary to and capable of forming dsRNA complexes with a "sense" strand of mRNA. Hybridization of mRNA inhibits its translation into proteins, thus, antisense mRNA acts as a very specific protein synthesis inhibitor. Antisense mRNA may be protective, if it complements for example a viral protein mRNA or mRNA transcribed from an active oncogene. Antisense mRNA may be destructive, for example where it complements an essential host cell enzyme, such as a house-keeping enzyme with no effective alternate pathway, or renders the host cell susceptible to agents which inhibit the alternate pathways. See also G. Zon et al, EP 288,163, which disclosed the use of oligodeoxynucleotides for inhibition of retroviral replication and oncogenic proliferation.

The term "ribozyme" refers to a catalytic RNA polynucleotide capable of catalyzing RNA cleavage at a specific sequence. Ribozymes are useful for attacking particular mRNA molecules. For example, in chronic myelogenous leukemia, a chromosomal translocation involving the genes bcr and abl (Philadelphia chromosome) results in expression of a bcr-abl fusion protein, which is believed to result in abnormal function of the abl oncoprotein. Because the fusion between the bcr and abl genes occurs at points within one of two introns, the spliced bcr-abl fusion transcript contains only two possible sequences at the splice junction between the bcr and abl exons. As the bcr-abl mRNA will only occur in lymphoid cells which have undergone this oncogenic chromosome translocation, a ribozyme specific for either of the two bcr-abl fusion mRNA splice junctions may be prepared, and thus may inhibit expression of the corresponding oncoprotein.

The term "vector" as used herein refers to any polynucleotide construct capable of encoding the cis-acting regulatory sequence and the effector gene(s) selected, and capable of transferring these genes into suitable target cells. Vectors may be linear or circular, double stranded or single stranded. Vectors may comprise DNA, RNA, DNA/RNA hybrids, and DNA and/or RNA polynucleotides having chemically modified bases. Suitable vectors within the scope of this invention include linear dsDNA segments, plasmids, recombinant viruses (e.g., recombinant vaccinia, adenovirus, adeno-associated viruses, and the like), replication-defective retroviral vectors (including human, simian, murine, and the like), suitably non-pathogenic derivatives of replication-competent retroviral vectors, and the like. Replication defective retroviral vectors are presently preferred.

B. General Method

Preparation of polynucleotide constructs is conducted using methods known generally in the art. Once an infectious agent or hyperproliferative disorder has been selected for treatment, the first step is to identify an associated trans-acting factor, an appropriate cis-acting sequence, and an effector gene.

Some viral trans-acting factors are already known and characterized. Other viral trans-acting factors may be identified by deletion analysis of the cloned viral genome. For example, a new virus may be cloned and sequenced using standard techniques, and the open reading frames identified. Then, deletion mutants are prepared using restriction enzymes, and the mutant viruses assayed for transcriptional competence in suitable host cells. Mutants which exhibit very low mRNA transcription probably lack either a gene encoding a trans-acting factor, or a cis-acting regulatory sequence. Whether the deletion affects the trans-acting factor or the cis-acting sequence can generally be determined by examination of the position and content of the genomic sequence (e.g., cis-acting viral regulatory sequences are generally found upstream of open reading frames). The sequence of the cis-acting viral region may be compared for homology to known cis-acting regions. As homologous cis-acting sequences may react with the same trans-acting factor, appropriate endogenous trans-acting factors may thus be identified. Alternatively, viral proteins may be expressed recombinantly in appropriate hosts (e.g., bacteria, yeast, mammalian cell culture), and purified extracts labeled and screened for binding to the viral genome library. In this manner, appropriate trans-acting factor/cis-acting sequence pairs may be identified. The suitability of the pair may be evaluated using the CAT expression assay detailed below and in the examples. In these assays, the cis-acting sequence is cloned into a suitable vector, and a suitable reporter gene (e.g., CAT, B-galactosidase, etc.) ligated to the cis-acting sequence to provide for cis-control. The test construct is then transferred into a suitable host cell (e.g., mammalian cell culture) and assayed for reporter gene expression in the presence and absence of the trans-acting factor. Suitable effector genes are known in the art, or may be cloned using standard techniques.

Intracellular parasites (including viruses) often induce interferon expression. Thus, isolation of the interferon cis-acting sequence should allow identification of trans-acting factors involved in the anti-parasite response, and preparation of appropriate polynucleotide constructs of the invention.

Hyperproliferative disorders are characterized by inappropriate gene regulation or gene product activity, typically involving cell growth or differentiation factors, and occasionally genes encoding structural proteins. Inappropriate gene regulation may result from the expression of a dysfunctional trans-acting factor (e.g., a factor in which truncation or mutation has eliminated inhibition of the factor, or which binds irreversibly, etc.), from the over-expression of a trans-acting factor or receptor (e.g., due to the translocational juxtaposition of a strong promoter), or other defects. In any case, the disorder characteristically exhibits a trans-acting factor which is either different from those found in normal cells, or is present in abnormally large quantities. Trans-acting factors encoded by viruses associated with hyperproliferative disorders (e.g., HTLV-I, HTLV-II, the E6 and E7 genes of HPV type 16 and type 18) may also be used to regulate expression of an effector gene, as described herein. Once the affected cis-acting sequence is identified, a suitable effector gene may be selected. As the characteristic trans-acting factors are generally at least somewhat homologous to normal trans-acting factors, the cis-acting sequence is likely to exhibit some regulation by endogenous trans-acting factor in normal cells. Thus, preferred effector genes for treatment of hyperproliferative disorders are those which are relatively non-toxic to the host cell at low levels. However, the activity of the trans-acting factors may be constitutively high in the hyperproliferative cells, whereas the activity may be lower and fluctuating (as during the cell cycle) in normal cells. This difference may be exploited to allow accumulation of high levels of effector gene product in hyperplastic cells.

Similarly, many cell-type specific trans-acting factors and cis-acting regulatory sequences have been discovered and described in the literature. Additional cis-acting regulatory sequences may be determined by the methods outlined above. It should be noted that in some instances, a trans-acting factor associated with a hyperproliferative disorder and its cis-acting regulatory sequence will be identical to normal, cell-type specific trans-acting factors and regulatory sequences. In such cases, the hyperproliferative disorder is typically caused by an excess concentration of trans-acting factor. Accordingly, the effector gene must be carefully selected.

Referring to FIG. 1, a generic retroviral vector of the invention is depicted. The vector comprises a 5' retroviral LTR and primer binding site (1), a psi encapsidation (packaging) signal sequence (2), an optional 3' RNA processing signal sequence (3), an effector gene (4), a 5' cis-acting regulatory sequence (5) including a promoter, optionally a promoter (6) and selectable marker gene (7), and a 3' retroviral LTR and primer binding site (8). Sequences 1–8 constitute the retroviral portion of the vector, while sequence 9 is typically derived from a plasmid, and provides for maintenance of the vector in cell culture. The 5' LTR (1) and 3' LTR (8) provide for reverse transcription and integration of the vector into the host cell genome. Suitable LTRs include those derived from Moloney murine leukemia virus (Mo-MuLV) (Shinnick et al, *Nature* (1981) 293:543), Harvey murine sarcoma virus (Ha-MSV), (Van Beveran et al, *Cell* (1981) 27:97), HTLV-I, HTLV-II, HIV-1, and HIV-2. In replication-defective retroviruses, the U3 region of the 3' LTR (8) is inactivated. Psi sequence (2) must be included in order for the vector to be included in viral capsids generating in the packaging cell line, but is otherwise inactive once integrated into the host genome. Suitable psi sequences have been described by Cepko et al, *Cell* (1984) 37:1053–62; Guild et al, supra; and Kriegler et al, *Cell* (1984) 38:483. Where the vector is nonretroviral, and is to be inserted by transfection rather than infection, the LTR sequences and psi sequence may be omitted. The effector gene (4) is as described above. In "internal promoter" recombinant retroviral vectors, the effector gene (4) is provided with its own promoter/cis-acting regulatory sequence (5) and terminator sequence/polyadenylation sequence (4) (although the terminator and PA sequences may be derived from the effector gene).

The effector gene may be oriented in either direction, but is usually oriented in the direction opposite to the LTR reading frame. In "enhancer replacement" recombinant retroviral vectors, the effector gene (4) is oriented in the same direction as the LTR, and is not provided with a separate cis-acting regulatory sequence (5) or terminator sequence/polyadenylation sequence (4). Instead, the cis-acting regulatory sequence is provided within the 3' LTR (8) U3 region, so that the effector gene is controlled by the cis-acting regulatory region only after reverse transcription.

The selectable marker (7), if present, encodes a characteristic which enables cells expressing the marker sequence to survive under conditions selecting for transfected cells. The selectable marker typically encodes an enzyme conferring resistance to an antibiotic, for example chloramphenicol, neomycin (Southern et al, *J Mol Appl Gen* (1982) 1:327–41), or hygromycin (Gritz et al, *Gene* (1983) 25:179–88). The selectable marker, when employed, is usually provided with its own promoter (6) which allows expression of the marker gene during selection of transfected/infected cells. Suitable marker gene promoters include the histone promoter, HSV-1 tk promoter, and the metallothionein promoter.

Sequence 9 is a polynucleotide maintenance sequence, which provides for the stable maintenance of the vector within producer cells. Typically, sequence 9 is derived from a plasmid, and provides an origin of replication (such as pBR322 ori, or the yeast 2 μ origin) and (usually) an antibiotic resistance marker. Suitable maintenance sequences include pXf3, pBR322, pUC18, pML, and the like. In the case of linear DNA segments used for targeted integration, the vector may be linearized at a point within sequence 9. The LTR regions 1 and 8 are replaced with sequences homologous to the sequence of desired targeted recombination. Sequence 2 is deleted. Sequence 9 includes polynucleotide sequences which provide for maintenance and replication in microbial hosts, and additionally includes a counter-selection marker (which provides for deletion of transfected host cells which undergo non-specific integration).

Development of drug activation systems

As a prototype system for activation of cytotoxic drugs, we chose the thymidine kinase gene from Herpes Simplex Virus type 1 (HSV-1 tk). HSV-1 tk can activate a variety of dideoxynucleoside analogues (ddNs) by conversion of these drugs to the (5') monophosphate species. The ddNMPs can act as competitive inhibitors of cellular nucleotide or nucleoside kinases, causing depletion of cellular nucleotide pools; following conversion to triphosphate species by cellular enzymes, ddNTPs can be incorporated into nascent DNA (and possibly RNA) strands, causing chain termination.

One of the best-characterized ddNs which can be activated by HSV-1 tk is acyclovir (acyclo-G). The safety and efficacy of acyclovir derives primarily from its selective activation by HSV-1 tk: acyclo-G is converted to acyclo-GMP several thousandfold more efficiently by HSV-1 thymidine kinase (tk) than by cellular thymidine kinases (Km for HSV-1 tk=0.005 X Km Vero tk; Vrel HSV-1 tk=3,000,000 X Vrel Vero tk). Cellular enzymes then convert acyclo-GMP to acyclo-GTP, which is incorporated into DNA by HSV-1 DNA polymerase causing termination of viral DNA synthesis. Acyclo-GTP inhibits HSV-1 DNA synthesis at about ½₀ the concentration required for similar inhibition of cellular DNA synthesis (P. A. Furman et al, *J Virol* (1979) 32:72–77).

Once a cis-acting regulatory sequence has been identified, it is tested for effect in a model system. For example, the cis-acting regulatory sequence may be cloned into a plasmid with a suitable reporter gene, such as CAT or β-galactosidase. The plasmid is then transfected into a suitable cell line (e.g., CHO cells, HeLa, HUT78, and the like). The trans-acting factor may be supplied by selecting a host cell line which expresses the trans-acting factor, or by cotransfecting the host cell line with a plasmid encoding the trans-acting factor under control of a different promoter (either inducible or constitutive). The transfected host cells are then assayed for expression of the reporter gene.

The suitability of an effector gene such as HSV-1 tk is assessed by cloning into a suitable plasmid under control of the selected cis-acting regulatory region. The plasmid also preferably contains a selectable marker, allowing one to select those cells which have become genetically transformed by the vector.

General structure of thymidine kinase vectors

The general structure of retroviral vectors which can be used to generate recombinant retroviruses containing an effector gene linked to cis-acting regulatory elements is shown in FIG. 1. The basic retroviral vectors for expression of HSV-1 tk are derived from Moloney Murine Leukemia Virus (Mo-MuLV). All of the Mo-MuLV genes (gag, pol and env) have been removed from the vectors in order to generate completely replication-defective viruses. The remaining components are required for expression and packaging of viral RNA, reverse transcription and integration, and transcription of the tk gene (and marker gene, if desired) in the target cells. These components consist of the Mo-MuLV Long Terminal Repeats (LTRs), the plus- and minus-strand primer binding sites, and the RNA encapsidation signal (Psi sequence).

In order to regulate the expression of HSV-1 tk in a cell type-specific manner, a hybrid transcription unit is constructed in which the HSV-1 tk coding sequence replaces the coding sequence of a cell type-specific transcription unit.

Expression of the HSV-1 tk gene via these vectors can be accomplished in two ways. The first type of vector uses a separate enhancer/regulatory element to regulate expression of HSV-1 tk. In this type of vector, transcription of HSV-1 tk proceeds in the opposite orientation to the plus-sense of the provirus (as shown in FIG. 1). The tk gene is provided with its own polyadenylation signal, and, if desired, also can be provided with an intron between the tk coding sequence and polyadenylation signal. Potential transcriptional interference in this first class of vectors can be reduced by removing the enhancer/regulatory element sequences from the 3' LTR of the vector. Because only the U3 sequences of the 3' LTR are transcribed into viral RNA, these sequences form both LTRs in the resultant provirus. This allows integration of the proviral cDNA, but results in loss of the enhancers and regulatory elements from both LTRs of the provirus.

In the second type of vector (enhancer replacement vector), the Mo-MLV LTR provides the enhancer and regulatory element sequences that control expression of the HSV-1 tk gene. The Mo-MLV LTR can drive expression of heterologous genes in a variety of cell types (excluding hematopoietic stem cells), but is most efficient in T-cells. Control of cell type-specific gene expression of HSV-1 tk may be achieved by substitution of specific enhancer/regulatory element sequences for the enhancer/regulatory element sequences within the 3' Mo-MLV LTR. The 5' Mo-MLV LTR is retained in the vector to allow efficient expression of viral RNA in the packaging cell line used to generate infectious virus.

A selectable marker gene can be incorporated into these vectors 3' to the HSV-1 tk gene in order to allow in vitro selection of transformed cells. Expression of the marker gene is provided by its own regulatory element. In general, this regulatory element would be derived from a moderately active cellular gene that is constitutively expressed in all tissues. Some examples of such regulatory elements would be the cytoplasmic β actin promoter, histone promoters, and promoters for glycolytic enzymes.

The second type of vector uses a separate enhancer/regulatory element to regulate expression of HSV-1 tk. In this type of vector, transcription of HSV-1 tk proceeds in the opposite orientation to the plus-sense of the provirus. The tk gene is provided with its own polyadenylation signal, and, if desired, also can be provided with an intron between the tk coding sequence and polyadenylation signal. Potential transcriptional interference in this second class of vectors can be reduced by removing the enhancer/regulatory element sequences from the 3' LTR of the vector. This allows integration of the proviral cDNA, but results in loss of the enhancers and regulatory elements from both LTRs of the provirus.

A selectable marker can be provided, as in the first class of vectors, and is transcribed in the opposite direction from HSV-1 tk. Transcription thus initiates in the center of the integrated provirus and proceeds in opposite directions, in a manner analogous to the transcription of the E2/E3 genes of human adenoviruses.

Formulation and Administration

The polynucleotide constructs of the invention may be formulated, depending on the form of construct. For example, where the vector is a competent (infectious) virus, it may be formulated in the same manner as live virus vaccines. Such formulations are typically buffered, physiologic saline for injection, or buffered oral formulations, either of which may optionally contain antibiotics. Liposome formulations may be prepared by standard methods, for example by suspending lipids in chloroform, drying the lipids onto the walls of a vessel, and hydrating the lipids with a solution containing the polynucleotide construct. Suitable lipids are known in the art, including phosphatidyl serine, phosphatidyl glycerol, lethicin, and the like. A synthetic lipid particularly useful for polynucleotide transfection is N-[1-(2,3-dioleyloxy)propyl]-N,N,N-tri-methylammonium chloride, which is commercially available under the name Lipofectin® (available from BRL, Gaithersburg, Md.), and is described by P. L. Felgner et al, *Proc Nat Acad Sci USA* (1987) 84:7413.

Recombinant retroviral vectors may also be formulated for in vivo administration (if replication defective). Vectors which are based on HIV-1 or HIV-2 will demonstrate the same cellular tropisms as the native virus, thus providing an efficient and comprehensive means for targeting the appropriate cell populations in vivo when treating HIV-1 or HIV-2 infection. Vectors based on HIV may employ the HIV LTR promoters, tar sequence, and the tat gene for control of expression of heterologous genes. One may refine the target cell specificity of the vector by an appropriate choice of packaging constructs (e.g., env gene). For example, the isolate HIV-$1_{SF162}$ (M. Quiroga et al, "Modern Approaches to New Vaccines" (1989, Cold Spring Harbor Laboratories) p. 80) is naturally selective for macrophage infection: thus, by packaging the vector in an HIV-$1_{SF162}$-derived envelope, targeting to the macrophages can be effected. Similarly, packaging the vectors using recombinant envelope genes which incorporate sequences derived from envelopes or capsids derived of hepatitis B virus (or HAV, or HCV) to obtain targeted delivery to hepatocytes. By using a packaging cell line expressing envelope proteins derived from HIV-2, one can obtain an effective method for targeting the vectors of the invention for protection of TH-cells, due to the affinity of gp$160^{env}$ for CD$4^+$ (Smith et al, *Science* (1987) 238:1704–06).

The mode of administration of polynucleotide constructs of the invention depends on the nature of the vector. For example, retroviral vectors may be administered by inoculation, parenterally or orally. Where the vector is an infectious recombinant virus, administration may be by parenteral injection, oral or intranasal administration, and the like. Liposome formulations are preferably administered by intranasal spray or intravenous injection. The presently preferred method of administration is by incubating defective retroviral vectors with aspirated autologous bone marrow cells or T lymphocytes ex vivo, followed by reintroduction of the treated cells by standard techniques. Briefly, bone marrow cells are aspirated by techniques known in the art for bone marrow transplants, and are generally aspirated from the pelvis. If desired (particularly in the treatment of leukemia and other hyperplastic disorders), the subject may be treated with chemotherapy or radiotherapy following bone marrow aspiration, in order to reduce the burden of infected or hyperproliferating cells. The aspirate may be screened to remove undesirable material (e.g., tumor cells, bacteria, viral particles, and the like), for example by immunoprecipitation, immunoadsorption, immunoreaction with complement fixation, fluorescence-activated cell sorting (FACS), and the like. Ideally, hematopoietic stem cells are labeled and isolated using stem cell-specific MAbs. The screened aspirate is then transfected or infected with a construct of the invention. One method of infection is to maintain the aspirated cells in culture in contact with infectious titers of replication-defective retroviral vectors for a period sufficient to insure efficient inoculation. Growth factors for hematopoietic cells (for example IL-3) may be added during cocultivation (E. A. Dzierzak, supra). The calcium phosphate transfection techniques known for murine cells may be used (see for example, E. A. Dzierzak, supra; S-F. Yu et al, *Proc Nat Acad Sci USA* (1986) 83:3194–98). Constructs may also be introduced by electroporation (S. Mansour, supra). Alternatively, one may employ a transfection agent such as Lipofectin®. Where the vector includes a marker, the infected cells may be screened or selected, if desired. The infected cells are then reintroduced into the subject using methods employed for autologous bone marrow transplantation, typically by intravenous infusion or injection. One may also transfect or infect lymphocytes either in vivo or ex vivo using constructs of the invention. Infection using MLV-based constructs is preferably conducted ex vivo, as the envelope is inactivated by human complement. Specific subsets of the lymphocyte population may be selected by employing monoclonal antibodies to separate the desired subset, or by other methods known in the art: see for example P. W. Kantoff et al, *Proc Nat Acad Sci USA* (1986) 83:6563–67.

If desired, one may convert some of the lymphocytes or bone marrow cells to packaging cells, by inserting independent constructs capable of expressing the viral genes encoding gag-pol and env, followed by insertion of a vector of the invention. O. Danos et al, *Proc Nat Acad Sci USA* (1988) 85:6460–64. When the autologous packaging cells are reintroduced into the subject, continuous expression of replication-defective retrovirus during the cell lifetime results in transfer of the therapeutic construct of the invention to a large number of host cells.

C. Examples

The examples presented below are provided as a further guide to the practitioner of ordinary skill in the art, and are not to be construed as limiting the invention in any way.

EXAMPLE 1

Recombinant Retroviral Vectors

Retroviral vectors were constructed using standard techniques for manipulation of recombinant DNA (T. Maniatis et al., *Molecular Cloning: A Laboratory Manual* (New York, Cold Spring Harbor Laboratory, 1982)). Plasmids used in construction of retroviral vectors were obtained from the following sources: pMX1112SVNeo was a gift from M. McMann (UCSF), SV-N was a gift from E. Gilboa (constructed as described by Yu, supra).

Figure 2:
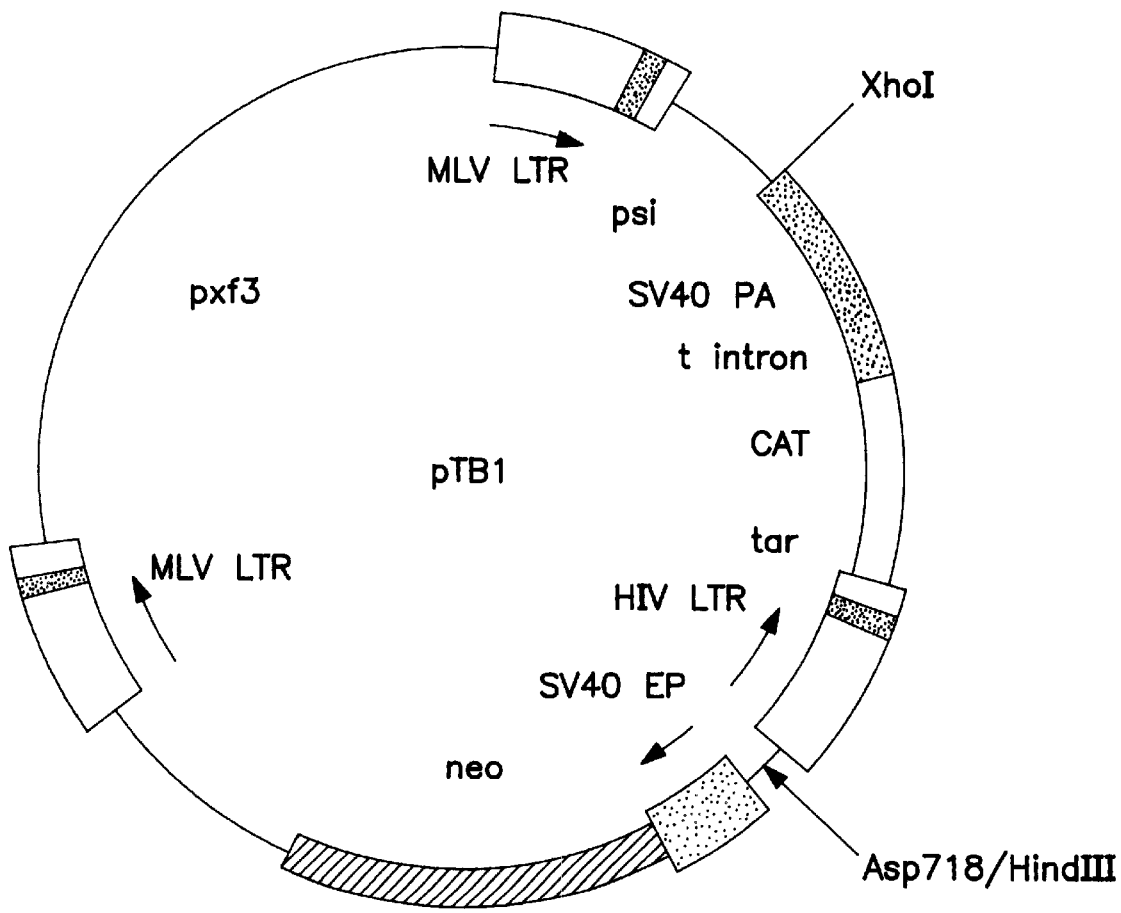
FIG. 2 is a diagram of the vector pTB1.
Figure 3:
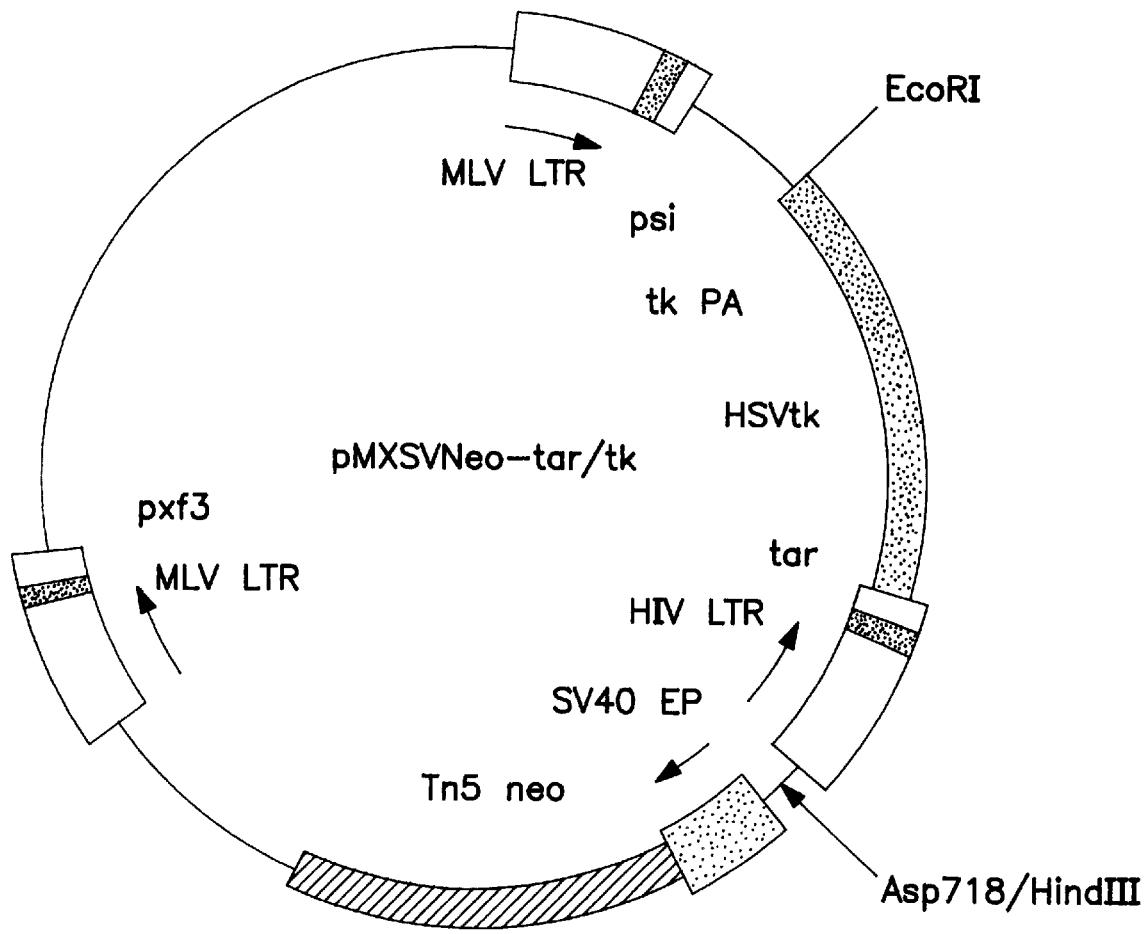
FIG. 3 is a diagram of the vector pMXSVNeo-tar/tk.

Plasmid pMX1112SVNeo is constructed by inserting a Cla—Cla fragment of the SV40 early promoter linked to the neo$^r$ gene into the plasmid pMX1112 (described by A. M. C. Brown et al, "Retroviral Vectors", pp. 189–212, in "DNA Cloning: a practical approach, vol. 3 (D. M. Glover, ed, IRL Press, 1987)). The SV40-neo$^r$ gene is positioned between the psi packaging sequence and the 3' Mo-MuLV LTR region on the plasmid. Plasmid pMXSVNeo18 was prepared from pMX1112SVNeo by removing the EcoRI site upstream of the 5' Mo-MuLV LTR, inserting an EcoRI linker at the XhoI site, and adding the pUC18 polylinker between the new EcoRI site and the HindIII site. Plasmid pTAR1 contains the HIV 5' LTR (including the tar sequence), a gene encoding CAT, and an SV40 polyadenylation signal and t intron, and was constructed by cloning the XhoI-NarI fragment of HIV-1 (SF2) (R. Sanchez-Pescador et al, *Science* (1982) 227:484–92) into pML. A synthetic polylinker was added at the NarI site, and the Stu1-BamHI fragment of pSV2CAT (C. M. Gorman et al, *Proc Nat Acad Sci USA* (1982) 79:6777–81) containing the CAT gene and SV40 RNA processing signals was inserted to provide pTAR1. The pTAR1 was cleaved with Asp718 and XhoI, and the resulting fragment cloned into pMXSVNeo18 to produce pTB1, shown in FIG. 2. Plasmid pTAT1 was constructed with the HIV tat gene under control of the SV40 EP, and flanked by the SV40 polyadenylation signal (Peterlin et al, supra). Plasmid pRT contains the HSV-1 tk gene, promoter, and RNA processing signals. The plasmid ptar/tk was prepared by cloning the BglII-EcoRI fragment of pRT (containing the tk coding sequence and polyadenylation signal) into pTAR1 in place of the CAT gene. Plasmid pMXSVNeo-tar/tk was constructed by cloning the Asp718-EcoRI portion of ptar/tk into the pMXSVNeo18 polylinker (pMXSVNeo-tar/tk is depicted in FIG. 3).

Amphotropic retroviruses capable of infecting human cells were prepared by standard techniques (R. Mann et al, *Cell* (1983) 33:153–59). Briefly, the amphotropic packaging cell line PA-317 (Miller et al, *Mol Cell Biol* (1986) 6:2895–902; ATCC CRL 9078) was transfected with plasmid vector using the $CaPO_4$ coprecipitation technique (R. Graham et al, *Virol* (1973) 52:456–67). 10 µg of plasmid vector plus 25 µg salmon sperm DNA carrier were applied as a $CaPO_4$ coprecipitate to $5 \times 10^5$ PA-317 cells in a 60 mm tissue culture dish for 8–16 h. The precipitate was removed and the monolayer was rinsed with Dulbecco's phosphate-buffered saline. Fresh medium (Dulbecco's modified Eagles medium, DMEM, supplemented with 10% fetal bovine serum and antibiotics) was applied and the cells were allowed to grow and recover for 2 d. The transfected cells were then trypsinized and transferred to a 150 mm2 T-flask and grown for 10–14 d in medium containing 0.8 mg/mL G418. The resulting G418-resistant colonies were trypsinized and cloned by limiting dilution in 96-well tissue culture plates. Recombinant retrovirus produced by individual clones was characterized by infection of human cell lines (HeLa, ATCC CCL 2: HUT78, ATCC TIB 161) to determine viral titer and generation of the correct proviral structure.

Ecotropic recombinant retroviruses were prepared as described above, except that the ecotropic packaging cell line Psi-2 (R. Mann, supra) was used instead of PA-317.

EXAMPLE 2

Infection Of Cells With Recombinant Retroviruses

Cell lines were infected with recombinant retroviruses using standard procedures (R. Mann, supra). Briefly, $5 \times 10^6$ cells were plated into 60 mm tissue culture dishes and allowed to grow for 16 h. Cell-free supernatants from packaging cells containing plasmid vectors was applied to the target cells for 6–8 h in the presence of 8 µg/mL polybrene. In the case of viruses carrying the G418-resistance marker, cells were grown, selected, and cloned as described for preparation of packing clones, above. Retroviruses carrying HSV-1 tk, but lacking the G418-resistance marker were titered using tk– cell lines: L-M (tk–) (ATCC CCL 1.3) for ecotropic viruses, 143 B cells (ATCC CRL 8303) for amphotropic viruses. Selection for $tk^+$ colonies was performed using HAT medium.

EXAMPLE 3

Assay For Trans-activation By HIV Tat

Plasmids pTAR1, pTB1, and pTB2 (having the HIV LTR region in the opposite orientation from pTB1), encoding CAT under control of the HIV tar cis-acting regulatory sequence, were transfected into HeLa cells. Plasmid pTAT1, expressing the HIV tat trans-acting agent, was transfected into half of the HeLa cells. After 48 hours, the cells were lysed, and $^{14}C$-chloramphenicol was incubated with the lysates. The products were extracted with EtOAc, and analyzed by thin-layer chromatography.

The results indicated that CAT was expressed in HeLa cells which contained both a tar-encoding plasmid and a tat-encoding plasmid, but not in HeLa cells lacking the pTAT1 plasmid. Although the level of constitutive expression (leakiness) varied little between pTAR1, pTB1, and pTB2, CAT expression in response to HIV tat was higher in cells containing pTB1 and pTB2 than in cells containing pTAR1 (lacking the Mo-MuLV LTRs and SV40 enhancer).

EXAMPLE 4

Antiviral Cytotoxic Effector Genes

Figure 5:
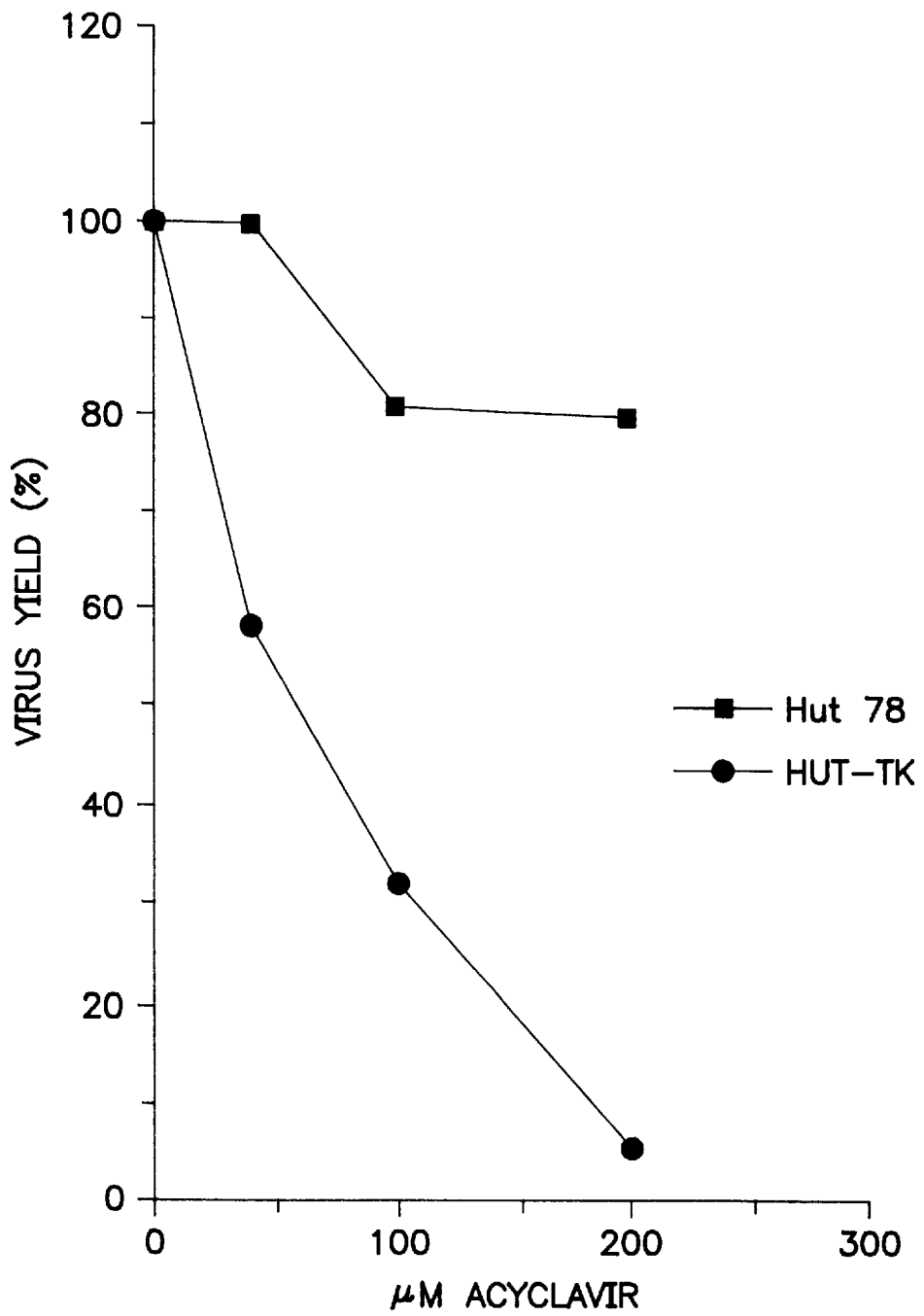
FIG. 5 graphically illustrates the results of the experiment described in Example 4.

Amphotropic MXSVNeo-tar/tk retrovirus was produced, and used to infect HUT78 cells (ATCC TIB 161). Transformed cells ("HUT-tk cells") were selected using 1 mg/mL G418. The sensitivity of mass-cultured HUT-tk cells to acyclovir was determined by growth in medium containing various concentrations of drug. HUT78 cells containing pMXSVNeo-tar/tk ("HUT-tk cells") were pelleted and exposed to polybrene (2 µg/mL) at 37° C. for 30 minutes. Cells were then pelleted and resuspended at $10^5$ cells per mL, and exposed to HIV-1 (SF2) for 1.5 hours at 37° C. The cells were then pelleted and resuspended in RPMI 1640 medium containing 10% fetal calf serum and antibiotics at 104 cells per 50 µL. Fifty µL of cell suspension was then distributed to wells of a 24 well plate containing 1 mL of medium with 45, 100, or 200 µM acyclovir. HIV-SF2 was added (sufficient to provide 3 OD in a p25 gag ELISA after 7 days of incubation), and was allowed to propagate for 7 days, and then assayed by anti-p25gag ELISA. Normal HUT78 cells served as controls for the effect of HSV-1 tk. The results of these experiments are shown in FIG. 5.

Although HIV replication in HUT78 cells was not significantly affected by acyclovir, replication was strongly inhibited by acyclovir in HUT-tk cells (about 60% with 100 µM acyclovir). Cytopathic/cytotoxic effects were apparent in both cell types (data not shown). Although analysis of single cell clones of HUT-tk showed variation in sensitivity to acyclovir, the mass-cultured HUT-tk cells were capable of significantly restricting viral replication.

EXAMPLE 5

Assay For Inhibition Of HIV Replication

HIV-infectable cells transformed to an HSV-1 tk positive phenotype can be used for screening nucleoside analogues for antiviral activity and cellular cytotoxicity (Mitsuya, supra).

HUT78 cells containing pMXSVNeo-tar/tk ("HUT-tk cells") were cloned by limiting dilution and assayed for sensitivity to varying concentrations of acyclovir as a measure of constitutive tk expression. An especially sensitive clone was designated TK.5, was chosen to test the ability of cells expressing high levels of tk to activate ZT and resist HIV infection.

HUT78, mass-cultured HUT-tk (from Example 4), and TK.5 cells were pelleted and exposed to polybrene (2 μg/mL) at 37° C. for 30 minutes. Cells were then pelleted and resuspended at $10^5$ cells per mL, and exposed to HIV-1 (SF2) for 1.5 hours at 37° C. The cells were then pelleted and resuspended in RPMI 1640 medium containing serum and antibiotics at $10^5$ cells per 50 μL. Fifty μL of cell suspension was then distributed to individual wells of a 24 well plate containing 1 mL of medium with 0, 1, 5, or 10 μM AZT. The infected cells were culture for 7 days, and virus replication was then assayed by anti-p25gag ELISA. The results are set forth in FIG. 4.

EXAMPLE 6

Construction Of Specific Thymidine Kinase Vectors

The structure of various retroviral vectors containing HSV-1 tk is shown in FIG. 1. The functional characteristics and therapeutic applications of these vectors are described below.

SIN-tar/tk-H4Neo: This vector employs the self-inactivating vector described by Yu, using the HIV tar cis-acting sequence and the HSV-1 tk effector gene, and containing neomycin resistance under control of the H4 histone promoter. This plasmid confers susceptibility to ddNs on cells infected with HIV.

SIN-CD4/tk (-H4Neo): This vector is identical to the SIN-tar/tk-H4Neo vector described above, except that the tar cis-acting sequence is replaced with the cis-acting sequence which promotes expression of CD4 antigen in TH cells. The histone promoter/neomycin resistance marker is optional. This vector confers susceptibility to ddNs on all $CD4^+$ cells. As the CD4 antigen is currently believed to be important in the mode of entry for HIV, this vector would also be useful in the treatment of HIV infection.

SIN-Mac1/tk (-H4Neo): This vector is like SIN-tar/tk-H4Neo, with the HIV tar cis-acting sequence replaced by the cis-acting sequence regulating Mac1 antigen expression in macrophages. The histone promoter/neomycin resistance marker is optional. This vector confers susceptibility to ddNs on all macrophages, which also serve as host cells to HIV.

SIN-tar/rA-H4Neo: This vector employs the HIV-1 tar cis-acting sequence, controlling the ricin A effector gene, using $neo^r$ as a selectable marker.

SIN-fos/ppt: This vector employs the self-inactivating vector described by Yu, using the fos oncogene cis-acting sequence (R. Treisman Cell (1986) 46:567–74) using a plant phosphotransferase effector gene. This vector, in combination with a ddN, would be useful in the treatment of fos-type malignancies.

SIN-pcna/tnf: This vector uses the cis-acting sequence regulating Proliferating Cell Nuclear Antigen (described by J. E. Selis, Leukemia (1988) 2:561–601) and a tumor necrosis factor effector gene. Although PCNA is expressed in all cells, the expression is transient, and occurs only during cell division. Thus, normal cells infected with the vector would not produce toxic concentrations of TNF, whereas neoplastic hyperproliferating cells which are constantly in cell division would express toxic concentrations.

SIN-acg/ifn: This vector employs the cis-acting regulatory sequence which provides expression of α chorionic gonadotropin (S. E. Goelz, Science (1985) 228:187–90) in combination with a β-interferon effector gene. This vector, like the preceding vector, relies on the fact that acg is infrequently expressed in normal cells, and would be useful in cancer treatment.

SIN-IgG/Rbz: This vector employs the cis-acting sequence from IgG, along with a ribozyme effector gene specific for the bcl/abl splice site which occurs in chronic myelogenous leukemia (CML). As IgG is expressed in B-cells, cell-type protection against CML is obtained.

SIN-e7/Ld: This vector uses the cis-acting sequence responding to the E7 gene of human papilloma virus type 16 (HPV16) in conjunction with a Leishmania donovani purine 2'-deoxyribonucleosidease gene. As expression of HPV16 E7 gene is associated with carcinoma of the uterine cervix (Phelps et al, Cell (1988) 53:539–47), this vector (in combination with the drug 6-methylpurine 2-deoxyriboside) destroys cells in which the E7 gene is expressed.

HIV-2/tk: This vector is derived from HIV-2 from which all of the internal genes are deleted except for the portion of the gag gene which overlaps the psi (encapsidation) signal and the rev-response element from the env gene. The HSV-1 tk gene is inserted 3' from the psi sequence, and is expressed under control of the HIV-2 LTR. If desired, the HIV-1 tar sequence can be substituted for the HIV-2 tar sequence. This vector may be used to express HSV-1 tk from a genome-length RNA by deleting or altering the HIV gag sequence ATG codons (Guild et al, supra), obtaining expression of the HSV-1 tk gene from its own ATG start codon. Alternatively, one may include the HIV-2 env splice acceptor just 5' of the HSV-1 tk gene, without altering the gag start codons, thus obtaining expression of the HSV-1 tk via a spliced subgenomic mRNA. In either case, expression of HSV-1 tk is dependent upon complementation by tat from either a resident HIV-1 provirus or a superinfecting HIV-1 virus. Expression of tk in combination with administration of ACV or GCV then activates toxic levels of the antiviral agent, thus destroying the infected cell. These constructs may be packaged in either HIV-2 envelopes or in HIV-$1_{SF162}$ envelopes, the latter being useful for targeting and destroying infected macrophages.

Figure 4:
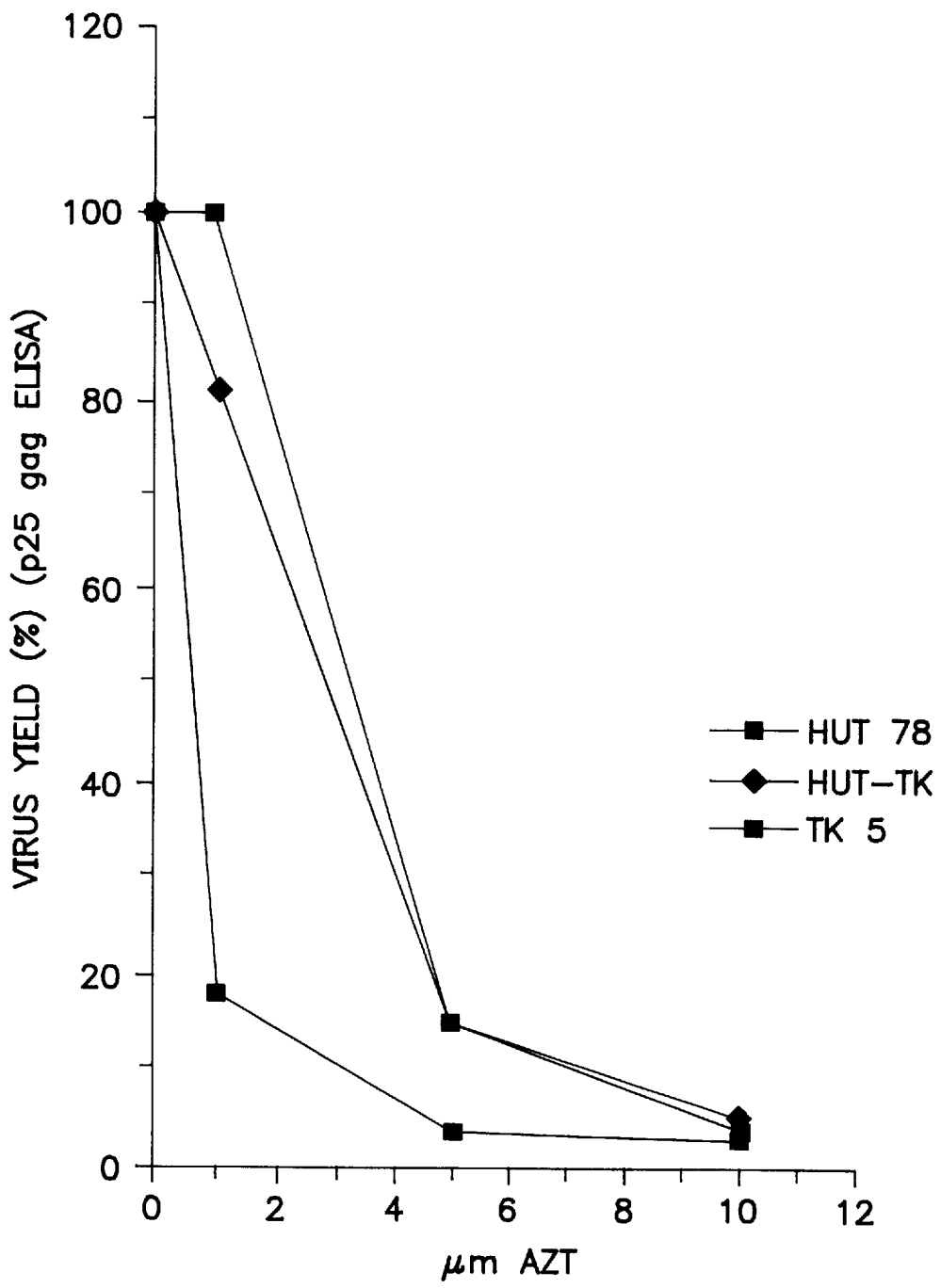
FIG. 4 graphically illustrates the results of the experiment described in Example 5.

HIV-2/TCR-tk: This construct incorporates the T-cell receptor promoter internally to drive expression of HSV-1 tk, and contains the RRE from env and psi signal from the 5' end of the HIV-2 gag gene. The 3' LTR of the vector is modified by inserting the TCR a constant region enhancer sequence (described by Ho et al, Proc Nat Acad Sci USA (1989) 86:6714), according the principle disclosed by J. Overhauser et al, J Virol (1985) 54:133–34 for construction of a glucocorticoid-responsive MOMLV. The HIV-2/TCR-tk vector may be used to infect and genetically transform $CD4^+$ cells in vivo. As neither the vector nor the T4 cell normally contains tat, no expression of transcripts initiating in the viral LTR occurs in the absence of infection with HIV. Initiation of transcription (expression of tk) occurs from the internal TCR promoter. Expression from this promoter is enhanced by the presence of the TCR a enhancers incorporated into the proviral LTRs. This vector provides constitutive expression of tk in the genetically transformed $T_H$ lymphocytes, which in turn activates an antiviral agent (e.g., ACV, ddC and the like). This permits the use of ACV and related compounds in cells in which they would normally not be effective. It also increases the effectivness of AZT at low concentrations as shown in FIG. 4. The ability to employ a variety of antiviral agents should reduce the possibility of development of drug resistance by HIV. An analogous vector may be prepared by substituting MLV virus components for the HIV sequences used, and employing an MLV amphotropic packaging cell line.

EXAMPLE 7

In Vivo Administration Of Constructs (A) Packaging cell lines for HIV-based vectors are constructed as follows:

The gag-pol coding sequence is isolated from HIV-1 or HIV-2, and is inserted into an expression vector under control of the human cytomegalovirus (CMV) major immediate early (MIE) promoter. A suitable polyadenylation sequence is provided 3' from the gag-pol insertion, for example, the SV40 polyA coding sequence. Both the gag-pol and the env sequences must contain the rev-response element (RRE) present in the env coding region, in order to obtain nuclear export (M. H. Malim et al, *Nature* (1989) 338:254–57).

The env sequence (including the RRE), which will determine the ultimate specificity of the finished vector, is obtained from a selected HIV-1, HIV-2 or SIV-1 isolate, and is inserted into a separate expression vector under control of the CMV MIE promoter. In this construction, a β-globin polyA sequence is employed. An intron may be inserted 5' to the env coding sequence, optionally containing a coding sequence for a marker or reporter gene (e.g., neo$^r$).

Separate similar vectors are constructed to insert tat cDNA and rev cDNA, under control of the SV40 early promoter. These vectors employ SV40 polyA sequences. By separating the coding sequences for gag-pol, env, tat, and rev, the possibility of recombination to regenerate a functional HIV virus is minimized.

The expression vectors are then used to construct a packaging cell line, by transfection of suitable cell line, for example NIH-3T3, HeLa, or the like. Upon transfection with a retroviral vector of the invention such as HIV-2/TCR-tk, a protective construct of the invention is prepared which is capable of infecting the population of host cells that is infected during bona fide HIV infection (mainly TH cells). When administered in combination with suitable antiviral agents such as AZT, ACV, ddC or the like, this treatment protects infected cells from infectious HIV replication.

(B) Macrophage/monocyte-trophic constructs are prepared following the procedure of part A above, but employing the HIV-1$_{SF162}$ env gene to provide env protein. Upon transfection with a vector of the invention such as HIV-2/tk, an ablative construct is provided which is capable of superinfecting and destroying host cells which are reservoirs of HIV and infection, particularly macrophages and monocytes.

What is claimed:

1. A method for treating a host cell ex vivo to render the host cell protected from a hyperproliferative disorder or infection by an infectious agent or to destroy the host cell when said hyperproliferative disorder or infection arises, wherein said hyperproliferative disorder or infection is associated with expression in said host cell of a trans-acting regulatory factor, and wherein said trans-acting regulatory factor is capable of regulating expression of genes under the control of a cis-acting regulatory sequence, which method comprises:

inserting into said host cell a polynucleotide construct comprising said cis-acting regulatory sequence; and
   an effector gene under the control of the cis-acting regulatory sequence, wherein the effector gene is expressed in the presence of the trans-acting regulatory factor to provide an effector gene product which renders said host cell protected from said hyperproliferative disorder or infection, or participates in the destruction of said host cell when said hyperproliferative disorder or infection arises, said effector gene product being a cytokine.

2. A method for treating a host cell ex vivo to render the host cell protected from a hyperproliferative disorder, or to destroy the host cell when said hyperproliferative disorder arises, wherein said hyperproliferative disorder is associated with the expression in said host cell of a trans-acting regulatory factor, and wherein said trans-acting regulatory factor is capable of regulating expression of genes under the control of a cis-acting regulatory sequence, which method comprises:

inserting into said host cell a polynucleotide construct comprising said cis-acting regulatory sequence, and an effector gene under the control of said cis-acting regulatory sequence, wherein said effector gene is expressed in the presence of the trans-acting regulatory factor and provides an effector gene product that renders said host cell protected from said hyperproliferative disorder, or that participates in the destruction of said host cell when said hyperproliferative disorder arises, said effector gene product being selected from the group consisting of a cytokine, a ribozyme, a glycosylation inhibitor, a myristylation inhibitor and an RNase.

3. The method of claim 2, wherein said effector gene renders the cell susceptible to destruction.

4. The method of claim 2 wherein said effector gene encodes a gene product which renders the host cell susceptible to protection.

5. A method for treating a host cell ex vivo to render the host cell protected from a hyperproliferative disorder, wherein said hyperproliferative disorder is associated with the expression in said host cell of a trans-acting regulatory factor, and wherein said trans-acting regulatory factor is capable of regulating expression of genes under the control of a cis-acting regulatory sequence, which method comprises:

inserting into said host cell a polynucleotide construct comprising said cis-acting regulatory sequence, and an effector gene under the control of said cis-acting regulatory sequence, wherein said effector gene is expressed in the presence of the trans-acting regulatory factor and provides an effector gene product that renders said host cell protected from said hyperproliferative disorder and, wherein said effector gene product comprises an antibody specific for an antigen associated with said hyperproliferative disorder.

6. The method of claim 4, wherein said effector gene product comprises a tumor necrosis factor, α interferon, β interferon, gamma interferon, transforming growth factor-β, or interleukin-2.

7. The method of claim 4, wherein said effector gene product comprises a protein which inhibits glycosylation or myristylation of proteins specific to said hyperproliferative disorder.

8. The method of claim 4, wherein said effector gene product comprises an RNase.

9. The method of claim 2 wherein said cis-acting regulatory sequence is present in at least two tandem copies.

10. The method of claim 2, wherein said effector gene further comprises operably linked to said gene:

(a) at least two copies of a polynucleotide binding sequence that competes for the binding of said trans-acting regulatory factor with a cis-acting regulatory site homologous to the polynucleotide binding sequence, and wherein transcription from the cis-acting regulatory site is associated with a hyperproliferative disorder; and
   (b) a strong terminator region.

11. The method of claim 1, wherein said infectious agent comprises HIV-1 or HIV-2, and said trans-acting regulatory factor comprises tat.

12. A polynucleotide construct which comprises:
a cis-acting regulatory sequence which is controllable by a trans-acting regulatory factor, wherein the presence of said trans-acting regulatory factor in a mammalian host cell is associated with that host cell having a hyperproliferative disorder or an infection by an infectious agent; and
an effector gene under the control of said cis-acting regulatory sequence, said effector gene encoding a gene product for rendering said host cell protected from said hyperproliferative disorder or said infection, or a gene product for destroying said host cell when said hyperproliferative disorder or said infection arises, said gene product being selected from the group consisting of a cytokine, a ribozyme, a glycosylation inhibitor, a myristylation inhibitor, and an RNase.

13. A polynucleotide construct which comprises: a cis-acting regulatory sequence, said cis-acting regulatory sequence controllable by a trans-acting regulatory factor, wherein the presence of said trans-acting regulatory factor in a mammalian host cell is associated with that host cell having a hyperproliferative disorder; and
an effector gene under the control of said cis-acting regulatory sequence and expressible in the presence of said trans-acting regulatory factor, said effector gene encoding a gene product, said gene product rendering said host cell protected from said hyperproliferative disorder, or said gene product participating in the destruction of said host cell when said hyperproliferative disorder arises, said gene product being a cytokine.

14. The construct of claim 13 which further comprises:
a polynucleotide maintenance sequence which provides for the stable maintenance of said construct within microbial cells.

15. The construct of claim 14 wherein said maintenance sequence is derived from a plasmid.

16. The construct of claim 13 wherein said polynucleotide construct comprises a recombinant viral vector which is vaccinia, HIV-1, HIV-2, adenovirus, or adeno-associated virus.

17. The construct of claim 15 wherein said plasmid is derived from a replication-defective retroviral vector.

18. The construct of claim 17 wherein said replication-defective retroviral vector further comprises a gene encoding a gp160$^{env}$ glycoprotein derived from HIV-1 or HIV-2.

19. The construct of claim 14 wherein said maintenance sequence is sequence 9.

20. A composition which comprises:
a polynucleotide construct according to claim 13; and
a pharmaceutically acceptable carrier.

21. The composition of claim 20 wherein said pharmaceutically acceptable carrier comprises a liposome.

22. The composition of claim 21 wherein said liposome further comprises antibodies specific for host cells desired to be treated.

23. The polynucleotide construct of claim 13, wherein said cytokine is a member of the group consisting of interferons, interleukins, tumor necrosis factor, transforming growth factors (α and β), epidermal growth factors and combinations thereof.

24. The polynucleotide construct of claim 23, wherein said cytokine is an interferon.

25. The polynucleotide construct of claim 24, wherein said interferon is α interferon, β interferon or gamma interferon.

26. The polynucleotide construct of claim 25, wherein said interferon is gamma interferon.

27. The polynucleotide construct of claim 23, wherein said cytokine is tumor necrosis factor.

28. A method for treating a host cell ex vivo to render the host cell protected from infection by an infectious agent, or to destroy the host cell when infected by said infectious agent, wherein said infection by said infectious agent is associated with the expression in said host cell of a trans-acting regulatory factor, and wherein said trans-acting regulatory factor is capable of regulating expression of genes under the control of a cis-acting regulatory sequence, which method comprises:
inserting into said host cell a polynucleotide construct comprising said cis-acting regulatory sequence and an effector gene under the control of said cis-acting regulatory sequence, wherein said effector gene is expressed in the presence of the trans-acting regulatory factor and the effector gene product renders said host cell protected from infection by said infectious agent, or participates in the destruction of said host cell when said host cell is infected by said infectious agent, said effector gene product being selected from group consisting of a cytokine, a ribozyme, a glycosylation inhibitor, a myristylation inhibitor and an RNase.

29. The method of claim 28, wherein said effector gene renders the cell susceptible to destruction.

30. The method of claim 28, wherein said effector gene encodes a gene product which renders the host cell susceptible to protection.

31. The method of claim 30, wherein said effector gene product comprises a cytokine that is tumor necrosis factor, α interferon, β interferon, gamma interferon, transforming growth factor-β, interleukin-2, or a combination thereof.

32. The method of claim 30, wherein said effector gene product comprises a protein which inhibits glycosylation or myristylation of infectious agent proteins.

33. The method of claim 30, wherein said effector gene product comprises an RNase.

34. The method of claim 28, wherein said cis-acting regulatory sequence is present in at least two tandem copies.

35. The method of claim 28, wherein said effector gene further comprises operably linked to said gene:
(a) at least two copies of a polynucleotide binding sequence which competes for the binding of said trans-acting regulatory factor with a cis-acting regulatory site homologous to the polynucleotide binding sequence and wherein transcription from the cis-acting regulatory site is associated with said infection by said infectious agent; and
(b) a strong terminator region.

36. The method of claim 35, wherein said infectious agent comprises HIV-1 or HIV-2, and said trans-acting regulatory factor comprises tat.

37. A polynucleotide construct which comprises: a cis-acting regulatory sequence, said cis-acting regulatory sequence controllable by a trans-acting regulatory factor, wherein the presence of said trans-acting regulatory factor in a human host cell is associated with said human host cell being infected by a human disease-causing infectious agent; and
an effector gene under the control of said cis-acting regulatory sequence and expressible in the presence of said trans-acting regulatory factor, said effector gene encoding a gene product capable of rendering said human host cell protected from infection by said infectious agent, or said gene product capable of participating in the infectious agent-specific destruction of said human host cell when said human host cell is infected by said infectious agent, said gene product further being selected from the group consisting of a cytokine, a glycosylation inhibitor, a myristylation inhibitor, and an RNase.

38. The construct of claim 37 which further comprises:
a polynucleotide maintenance sequence which provides for the stable maintenance of said construct within microbial cells.

39. The construct of claim 38 wherein said maintenance sequence is derived from a plasmid.

40. The construct of claim 37, wherein said polynucleotide construct comprises a recombinant viral vector which is vaccinia, HIV-1, HIV-2, adenovirus, or adeno-associated virus.

41. The construct of claim 39 wherein said plasmid is derived from a replication-defective retroviral vector.

42. The construct of claim 41 wherein said replication-defective retroviral vector further comprises a gp160$^{env}$ glycoprotein derived from HIV-1 or HIV-2.

43. The construct of claim 38 wherein said maintenance sequence is sequence 9.

44. The construct of claim 37 wherein said cis-acting regulatory sequence is capable of responding to HIV tat protein.

45. A composition which comprises:
a polynucleotide construct according to claim 66; and
a pharmaceutically acceptable carrier.

46. The composition of claim 45 wherein said pharmaceutically acceptable carrier comprises a liposome.

47. The composition of claim 46 wherein said liposome further comprises antibodies specific for host cells desired to be treated.

48. A polynucleotide construct which comprises a cis-acting regulatory sequence, said cis-acting regulatory sequence controllable by a trans-acting regulatory factor that is not encoded within said construct, wherein the presence of said trans-acting regulatory factor in a human host cell is associated with said human host cell being infected by a human disease-causing infectious agent; and
an effector gene under the control of said cis-acting regulatory sequence and expressible in the presence of said trans-acting regulatory factor, said effector gene encoding a gene product capable of rendering said human host cell protected from infection by said infectious agent, or said gene product capable of participating in the infectious agent-specific destruction of said human host cell when said human host cell is infected by said infectious agent, said gene product further being selected from the group consisting of a ribozyme, a glycosylation inhibitor, a myristylation inhibitor, and an RNase.

49. The construct of claim 48 which further comprises:
a polynucleotide maintenance sequence which provides for the stable maintenance of said construct within microbial cells.

50. The construct of claim 49 wherein said maintenance sequence is derived from a plasmid.

51. The construct of claim 48, wherein said polynucleotide construct comprises a recombinant viral vector selected from vaccinia, HIV-1, HIV-2, adenovirus, or adeno-associated virus.

52. The construct of claim 50, wherein said plasmid is derived from a replication-defective retroviral vector.

53. The construct of claim 52 wherein said replication-defective retroviral vector further comprises a gp160$^{env}$ glycoprotein derived from HIV-1 or HIV-2.

54. The construct of claim 49 wherein said maintenance sequence is sequence 9.

55. A polynucleotide construct for disease-specific expression which comprises a cis-acting regulatory sequence, said cis-acting regulatory sequence controllable by a trans-acting regulatory factor that is not encoded within said construct, wherein the presence of said trans-acting regulatory factor in a human host cell is associated with said human host cell being infected by a human disease-causing infectious agent; and
an effector gene under the control of said cis-acting regulatory sequence and expressible in the presence of said trans-acting regulatory factor, said effector gene encoding a cytokine capable of rendering said human host cell protected from infection by said infectious agent, or said gene product capable of participating in the infectious agent-specific destruction of said human host cell when said human host cell is infected by said infectious agent.

56. The polynucleotide construct of claim 55, wherein said cytokine is selected from the group consisting of interferons, interleukins, colony stimulating factors, transforming growth factors ($\alpha$ and $\beta$), epidermal growth factors and combinations thereof.

57. The polynucleotide construct of claim 56, wherein said cytokine is an interferon.

58. The polynucleotide construct of claim 57, wherein said interferon is a interferon, $\beta$ interferon or gamma interferon.

59. The polynucleotide construct of claim 58, wherein said interferon is gamma interferon.

60. The polynucleotide construct of claim 56, wherein said transforming growth factor is transforming growth factor $\beta$.

61. The polynucleotide construct of claim 56, wherein said interleukin is interleukin-2.

62. A polynucleotide construct which comprises: a cis-acting regulatory sequence, said cis-acting regulatory sequence controllable by a trans-acting regulatory factor, wherein the presence of said trans-acting regulatory factor in a human host cell is associated with said human host cell being infected by a human disease-causing infectious agent; and
an effector gene under the control of said cis-acting regulatory sequence and expressible in the presence of said trans-acting regulatory factor, said effector gene encoding a gene product capable of rendering said human host cell protected from infection by said infectious agent, or said gene product capable of participating in the destruction of said human host cell when said human host cell is infected by said infectious agent, said gene product further being selected from the group consisting of a cytokine, a ribozyme, a glycosylation inhibitor, a myristylation inhibitor, and an RNase.

63. A polynucleotide construct which comprises a cis-acting regulatory sequence, said cis-acting regulatory sequence controllable by a trans-acting regulatory factor that is not encoded within said construct, wherein the presence of said trans-acting regulatory factor in a human host cell is associated with said human host cell being infected by a human disease causing infectious agent; and
an effector gene under the control of said cis-acting regulatory sequence and expressible in the presence of said trans-acting regulatory factor, said effector gene encoding a gene product capable of rendering said human host cell protected from infection by said infectious agent, or said gene product capable of participating in the destruction of said human host cell when said human host cell is infected by said infectious agent, said gene product further being selected from the group consisting of a ribozyme, a glycosylation inhibitor, a myristylation inhibitor, and an RNase.

64. A polynucleotide construct for disease-specific expression which comprises a cis-acting regulatory sequence, said cis-acting regulatory sequence controllable by a trans-acting regulatory factor that is not encoded within said construct, wherein the presence of said trans-acting regulatory factor in a human host cell is associated with said human host cell being infected by a human disease-causing infectious agent; and an effector gene under the control of said cis-acting regulatory sequence and expressible in the presence of said trans-acting regulatory factor, said effector gene encoding a cytokine capable of rendering said human host cell protected from infection by said infectious agent, or said gene product capable of participating in the destruction of said human host cell when said human host cell is infected by said infectious agent.

65. A polynucleotide construct which comprises at least two of tandem copies of a cis-acting regulatory sequence, said cis-acting regulatory sequence controllable by a trans-acting regulatory factor that is not encoded within said construct, wherein the presence of said trans-acting regulatory factor in a human host cell is associated with said human host cell being infected by a human disease-causing infectious agent; and an effector gene under the control of said cis-acting regulatory sequence and expressible in the presence of said trans-acting regulatory factor, said effector gene encoding a gene product capable of rendering said human host cell protected from infection by said infectious agent, or said gene product capable of participating in the destruction of said human host cell when said human host cell is infected by said infectious agent, said gene product further being selected from the group consisting of an antisense mRNA that inhibits infection or inhibits expression of an essential host cell protein, a protease inhibitor, a ribozyme, a glycosylation inhibitor, a myristylation inhibitor, and an RNase.

66. A polynucleotide construct for disease-specific expression which comprises at least two tandem copies of a cis-acting regulatory sequence, said cis-acting regulatory sequence controllable by a trans-acting regulatory factor that is not encoded within said construct, wherein the presence of said trans-acting regulatory factor in a human host cell is associated with said human host cell being infected by a human disease-causing infectious agent; and an effector gene under the control of said cis-acting regulatory sequence and expressible in the presence of said trans-acting regulatory factor, said effector gene encoding a cytokine capable of rendering said human host cell protected from infection by said infectious agent, or said gene product capable of participating in the destruction of said human host cell when said human host cell is infected by said infectious agent.

67. A polynucleotide construct which comprises at least two tandem copies of a cis-acting regulatory sequence, said cis-acting regulatory sequence controllable by a trans-acting regulatory factor, wherein the presence of said trans-acting regulatory factor in a human host cell is associated with said human host cell being infected by a human disease-causing infectious agent; and an effector gene under the control of said cis-acting regulatory sequence and expressible in the presence of said trans-acting regulatory factor, said effector gene encoding a gene product capable of rendering said human host cell protected from infection by said infectious agent, or said gene product capable of participating in the destruction of said human host cell when said human host cell is infected by said infectious agent, said gene product further being capable of converting a prodrug into its active drug form.

68. The construct of claim 67 wherein said effector gene product is a nucleoside kinase capable of phosphorylating a dideoxynucleoside analogue at a greater rate than host cell nucleoside kinases.

69. The construct of claim 68 wherein said effector gene product is a nucleoside kinase that comprises a thymidine kinase.

70. The construct of claim 69, wherein said thymidine kinase comprises a herpes simplex thymidine kinase.

71. The construct of claim 70, which is pMXSVNeo-tar/tk.

72. The polynucleotide construct of claim 68, wherein said dideoxynucleoside analogue is acyclovir, AZT, gancyclovir, or dideoxycytidine.

73. A polynucleotide construct which comprises at least two tandem copies of a cis-acting regulatory sequence, said cis-acting regulatory sequence controllable by a trans-acting regulatory factor, wherein the presence of said trans-acting regulatory factor in a human host cell is associated with said human host cell having a hyperproliferative disorder; and an effector gene under the control of said cis-acting regulatory sequence and expressible in the presence of said trans-acting regulatory factor, said effector gene encoding a gene product capable of rendering said human host cell protected from said hyperproliferative disorder, or said gene product capable of participating in the destruction of said human host cell when said human host cell is in said hyperproliferative disorder, said gene product further being capable of converting a prodrug into its active drug form.

74. The construct of claim 73 wherein said gene product is a nucleoside kinase capable of phosphorylating a dideoxynucleoside analogue at a greater rate than host cell nucleoside kinases.

75. The construct of claim 74 wherein said nucleoside kinase comprises a thymidine kinase.

76. The construct of claim 75, wherein said thymidine kinase comprises a herpes simplex thymidine kinase.

77. The construct of claim 76, which is pMXSVNeo-tar/tk.

78. The polynucleotide construct of claim 74, wherein said dideoxynucleoside analogue is acyclovir, AZT, gancyclovir, or dideoxycytidine.

79. A polynucleotide construct for inhibiting infection by an infectious agent in a host cell, said construct comprising at least two copies of a polynucleotide binding sequence that competes for binding of a trans-acting regulatory factor against a cis-acting regulatory site that is homologous to said polynucleotide binding sequence, and wherein transcription from the cis-acting regulatory site is associated with an infection by said infectious agent.

80. A method for inhibiting infection by an infectious agent in a host cell, said method comprising:

administering to said host cell ex vivo a polynucleotide construct comprising at least two copies of a polynucleotide binding sequence that competes for binding of a trans-acting regulatory factor against a cis-acting regulatory site that is homologous to said polynucleotide binding sequence, and wherein transcription from the cis-acting regulatory site is associated with an infection in said host cell by said infectious agent.

81. The method of claim 80 wherein said infectious agent is a virus.

* * * * *